US008221750B2

(12) United States Patent
Solomon et al.

(10) Patent No.: US 8,221,750 B2
(45) Date of Patent: Jul. 17, 2012

(54) SINGLE CHAIN ANTIBODIES AGAINST β-AMYLOID PEPTIDE

(75) Inventors: Beka Solomon, Herzlia Pituach (IL); Rachel Cohen-Kupiec, Tel-Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 13/353,954

(22) Filed: Jan. 19, 2012

(65) Prior Publication Data

US 2012/0114650 A1      May 10, 2012

Related U.S. Application Data

(62) Division of application No. 12/064,144, filed as application No. PCT/US2006/032319 on Aug. 18, 2006, now Pat. No. 8,124,076.

(60) Provisional application No. 60/709,102, filed on Aug. 18, 2005.

(51) Int. Cl.
*A61K 39/395*    (2006.01)
*C07K 16/00*     (2006.01)
*C07K 16/18*     (2006.01)
*C07K 16/44*     (2006.01)

(52) U.S. Cl. ............... 424/130.1; 424/133.1; 424/135.1; 530/387.1; 530/387.3; 530/389.1

(58) Field of Classification Search .................. None
See application file for complete search history.

(56) References Cited

U.S. PATENT DOCUMENTS

2004/0044187 A1 *  3/2004  Sato et al. ................. 530/387.3
2008/0241884 A1   10/2008  Shitara et al.

FOREIGN PATENT DOCUMENTS

| EP | 1069185 A1 | 1/2001 |
| WO | 9951743 A1 | 10/1999 |
| WO | 02/074243 A2 | 9/2002 |
| WO | 2006/050041 A2 | 5/2006 |

OTHER PUBLICATIONS

Frenkel et al., N-terminal EFRH sequence of Alzheimer's beta-amyloid peptide represents the epitope of its anti-aggregating antibodies, Journal of Neuroimmunology, 88:85-90 (1998).

IPRP/Written Opinion from corresponding PCT International Application No. PCT/US2006/032319.

Winkler et al., Changing the antigen binding specificity by single point mutations of an anti-p24 (HIV-1) Antibody, Journal of Immunology, 165:4505-4514 (2000).

* cited by examiner

*Primary Examiner* — Jeffrey Stucker
*Assistant Examiner* — Stephen Gucker
(74) *Attorney, Agent, or Firm* — Browdy and Neimark, PLLC

(57) ABSTRACT

Anti-AβP scFvs and single domain antibodies were generated, and when these antibodies were displayed on filamentous phage or as soluble protein molecules, stabilized by the maltose binding protein, they could prevent the fibrilization of Aβp 1-40 and disaggregate Aβp 1-40 fibrils generated in vitro. The anti-Aβp scFv antibodies also stained amyloid neuritic plaques on slices from transgenic mice. The anti-AβP scFv and single domain antibodies can be used for inhibiting or treating Alzheimer's disease.

9 Claims, 15 Drawing Sheets

Linker-fwd primer
5'- TCAGGGGGAGGT*GCTAGC*GGTGGCGGAGGCTCTGA*IRTYKTGMTSACICA* -3' (SEQ ID NO:1)
3'-TGIIRISAGTGICAGAGRMGTCCACCTCGGCTCCCCTCCA*CGATCG*CCACCG -5' (SEQ ID NO:2)
linker-rev primer Linker sequence: GGTGGAGGGGATCAGGGGGAGGTGCTAGCGGTGGCGGAGGCTCT (SEQ ID NO:3)
Linker peptide    G G G G S G G G G A S G G G G S  (SEQ ID NO:4)

Fig. 1

RCK37 nucleotide sequence (750 nt)

ATGGCTCATGTCCAGTTTGTGCAGTCTGGGGGAGACTTAGTGAAGCCTGGAGGGTC
CCTGAAACTCTCCTGTGCAGCCTCTGGATTCACTTTCAGTAGCTATGGCATGTCTTG
GGTTCGCCAGACTCCAGACAAGAGGCTGGAGTGGGTCGCAACCATTAGTAGTGGT
GGTAGTTACACCTACTATCCAGACAGTGTGAAGGGGCGATTCACCATCTCCAGAG
ACAATGCCAAGAACACCCTGTACCTGCAAATGAGCAGTCTGAAGTCTGAGGACAC
AGCCATGTATTACTGTGCAAGACATAACTACGGTAGTAGCTACCCTTATGCTATGG
ACTACTGGGGTCAAGGAACCCCCGTCACCGTCTCTGCAGGTGGAGGCGGATCAGG
GGGAGGTGCTAGCGGTGGCGGAGGCTCTGAGATAATGATAACGCAGACTCCAGTA
ATCATGTCTGCATTTTCAGGGGAGAAGGTCACCATGACCTGCAGTGCCAGTTCAAG
TGTTAATTACATGCACTGGTATCAGCAGAAGTCAGGCACTTCCCCCAAAAAATGG
ATTTATGACACATCCAAATTGGCTTCTGGAGTCCCTGATCGCTTCAGTGGCAGTGG
GTCTGGGACCTCTTACTCTCTCACAATCAGCAGAATGGAGGCTGAAGATGCTGCCA
CTTATTACTGCCCGCAGTGGAGTAGTAACCCTCCCATGACGTTCGGTGGAGGCACA
AACCTGGAGATGAAACGCGCGGCCGCA (SEQ ID NO:5)

RCK37 amino acid sequence (250 aa)

MAHVQFVQSGGDLVKPGGSLKLSCAASGFTFSSYGMSWVRQTPDKRLEWVATISSGG
SYTYYPDSVKGRFTISRDNAKNTLYLQMSSLKSEDTAMYYCARHNYGSSYPYAMDY
WGQGTPVTVA<u>GGGGSGGGASGGGGS</u>EIMITQTPVIMSAFSGEKVTMTCSASSSVNYM
HWYQQKSGTSPKKWIYDTSKLASGVPDRFSGSGSGTSYSLTISRMEAEDAATYYCQQ
WSSNPPMTFGGGTNLEMKRAAA (SEQ ID NO:6)

Fig. 3A

ScFv RCK37 CDRs

Heavy Chain

CDR1 nt: AGCTATGGCATGTCT (SEQ ID NO:9)

aa: SYGMS (SEQ ID NO:10)

CDR2 nt: ACCATTAGTAGTGGTGGTAGTTACACCTACTATCCAGACAGTGTGAAGGGG (SEQ ID NO:11)

aa: TISSGGSYTYYPDSVKG (SEQ ID NO:12)

CDR3 nt: CATAACTACGGTAGTAGCTACCCTTATGCTATGGACTAC (SEQ ID NO:13)

aa: HNYGSSYPYAMDY (SEQ ID NO:14)

Light chain

CDR1 nt: AGTGCCAGTTCAAGTGTTAATTACATGCAC (SEQ ID NO:15)

aa: SASSSVNYMH (SEQ ID NO:16)

CDR2 nt: GACACATCCAAATTGGCTTCT (SEQ ID NO:17)

aa: DTSKLAS (SEQ ID NO:18)

CDR3 nt: CCGCAGTGGAGTAGTAACCCTCCCATGACG (SEQ ID NO:19)

aa: PQWSSNPPMT (SEQ ID NO:20)

Fig. 3B

RCK22 nucleotide sequence

ATGGCCCAGG TGCAGCTGCA GCAGTCTGGG GGAGGCTTAG TGCAGCCTGG
AGGGTCCCTG AAACTCTCCT GTGCAGCCTC TGGATTCACT TTCAGTAGGT
ATGGCATGTC TTGGGTTCGC CAGACTCCAG ACAAGAGGCT GGAGTTGGTC
GCAACCATTA ATAGTAATGG CGGTAGCACC TATTATCCAG ACAGTGTGAA
GGGCCGTTTC ACCATCTCCA GAGACAATGC AAGAACACC CTGTACCTGC
AAATGAGCAG TCTGAAGTCT GCGGACACAG CCATGTATTT CTGTGCCAGA
GGAGGTTACC TTGACTACTG GGGCCAAGGG ACCACGGTCA CCGTCTCCTC
AGGTGGAGGC GGTTCAGGCG GAGGTGGCTC TGGCGGTGGC GGAGCGGACA
TCGAGCTCAC TCAGTCTCCA TCTCTGGGAG AAAGTGTCAC CATCACATGC
CTGGCAAGTC AGACCATTGG TACATGGTTA GCATGGTTTC AGCAGAAACC
AGGGAAATCT CCTCAGCTCC TGATTTATGC TGCAACCAGC TTGGCAGATG
GGGTCCCATC AAGGTTCAGT GGTAGTGGAT CTGGAACAAA ATTTTCTTTC
AAGATCAGCA GCCTACTGGC TGAAGATTTT GTAACTTATT ACTGTCAACA
ACTCTACAGT ACTCCGTACA CGTTCGGAGG GGGGACAAAG TTGGAAATAA
AACGGGCGGC CGCA  (SEQ ID NO:7)

RCK22 amino acid sequence

MAQVQLQQSGGGLVQPGGSLKLSCAASGFTFSRYGMSWVRQTPDKRLELVATINSNGGST
YYPDSVKGRFTISRDNAKNTLYLQMSSLKSADTAMYFCARGGYLDYWGQGTTVTVSS<u>GGG</u>
<u>GSGGGGSGGGG</u>ADIELTQSPSLGESVTITCLASQTIGTWLAWFQQKPGKSPQLLIYAATS
LADGVPSRFSGSGSGTKFSFKISSLLAEDFVTYYCQQLYSTPYTFGGGTKLEIKRAAA (SEQ ID NO:8)

Fig. 3C

ScFv RCK22 CDRs

Heavy Chain

CDR1 nt: AGGTATGGCATGTCT (SEQ ID NO:21)

aa: RYGMS (SEQ ID NO:22)

CDR2 nt: ACCATTAATAGTAATGGCGGTAGCACCTATTATCCAGACAGTGTGAAGGGC (SEQ ID NO:23)

aa: TINSNGGSTYYPDSVKG (SEQ ID NO:24)

CDR3 nt: GGAGGTTACCTTGACTAC (SEQ ID NO:25)

aa: GGYLDY (SEQ ID NO:26)

Light Chain

CDR1 nt: CTGGCAAGTCAGACCATTGGTACATGGTTAGCA (SEQ ID NO:27)

aa: LASQTIGTWLA (SEQ ID NO:28)

CDR2 nt: GCTGCAACCAGCTTGGCAGAT (SEQ ID NO:29)

aa: AATSLAD (SEQ ID NO:30)

CDR3 nt: CAACAACTCTACAGTACTCCGTACACG (SEQ ID NO:31)

aa: QQLYSTPYT (SEQ ID NO:32)

Fig. 3D

SINGLE CHAIN ANTIBODIES AGAINST β-AMYLOID PEPTIDE

CROSS-REFERENCE TO RELATED APPLICATIONS

The present application is a divisional of application Ser. No. 12/064,144, filed Oct. 29, 2008 now U.S. Pat. No. 8,124,076, which claims the benefit of priority from provisional U.S. application No. 60/709,102, filed Aug. 18, 2005, the entire content of which is herein incorporated by reference.

BACKGROUND OF THE INVENTION

1. Field of the Invention

The present invention relates to antibodies for treating Alzheimer's patients.

2. Description of the Related Art

Beta amyloid peptide (Aβp), the product of processed amyloid precursor protein, is accumulated in the brains of Alzheimer patients for reasons that have not been elucidated yet. Immunotherapy towards Aβp is one approach researchers are using in looking for a relief or a cure for this disease. Antibodies generated towards the N-terminus of the beta amyloid peptide prevented the fibrilization of Aβp peptide in vitro, and significantly reduced the cytotoxic effects of Aβp fibrils on PC12 cells (Frenkel et al., 2000). Also, immunization with Aβ of transgenic mice that express the human amyloid precursor protein (APP) and exhibit Alzheimer's-like pathology, demonstrated that the mice developed humoral reaction towards the antigen, and exhibited a significant reduction in plaque load compared to controls (Schenk et al., 1999). Moreover, in these mice, active clearance of amyloid by microglial cells was noted. Bacskai et al. (2002) reported that FITC-labeled F(ab)$_2$ fragments of monoclonal anti-Aβ antibody or full-length antibody led to the clearance of 45% of the amyloid deposits in 18-month-old transgenic mice within 3 days. These results suggest that immunotherapy has the potential to either delay the generation of or reduce one of the major hallmarks of Alzheimer's pathology, i.e., Aβ plaques.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides single chain antibodies against β-amyloid peptide, which include the complementarity-determining regions of the heavy antibody chain and/or light antibody chain, preferably single chain (scFv) or single domain antibodies, and nucleic acid molecules and vectors encoding these anti-Aβp antibodies. Also provided are a host cell transformed with the nucleic acid molecule encoding the antibody against β-amyloid peptide and a method for producing and isolating such an antibody.

The present invention further provides a composition and a method for inhibiting or treating Alzheimer's disease by administering an anti-Aβp antibody of the present invention to a patient in need thereof.

BRIEF DESCRIPTION OF THE DRAWINGS

FIG. 1 shows the sequences of the linker forward (SEQ ID NO:1) and reverse (SEQ ID NO:2) primers, the linker sequence (SEQ ID NO:3) and the linker peptide sequence (SEQ ID NO:4).

FIGS. 3A-3D show the nucleotide and amino acid sequences of RCK37 (SEQ ID NOs:5 and 6; FIG. 3A) and RCK22 (SEQ ID NOs:7 and 8; FIG. 3C) along with their CDR nucleotide and amino acid sequences (SEQ ID NOs:9-32; FIGS. 3B and 3D).

FIG. 5A is staining with Q-RCK22, FIG. 5B is staining with Q-RCK37, and FIG. 5C is staining with Q-helper (no ScFv).

In FIG. 8A, the Tht emission values at 485 nm as a function of antibody added to the pre-aggregated β-amyloid are shown. The same results are shown in FIG. 8B except that the results are depicted relative to the level of Aβp 1-40 Tht emission which is considered 100% aggregated.

DETAILED DESCRIPTION OF THE INVENTION

Figure 2:
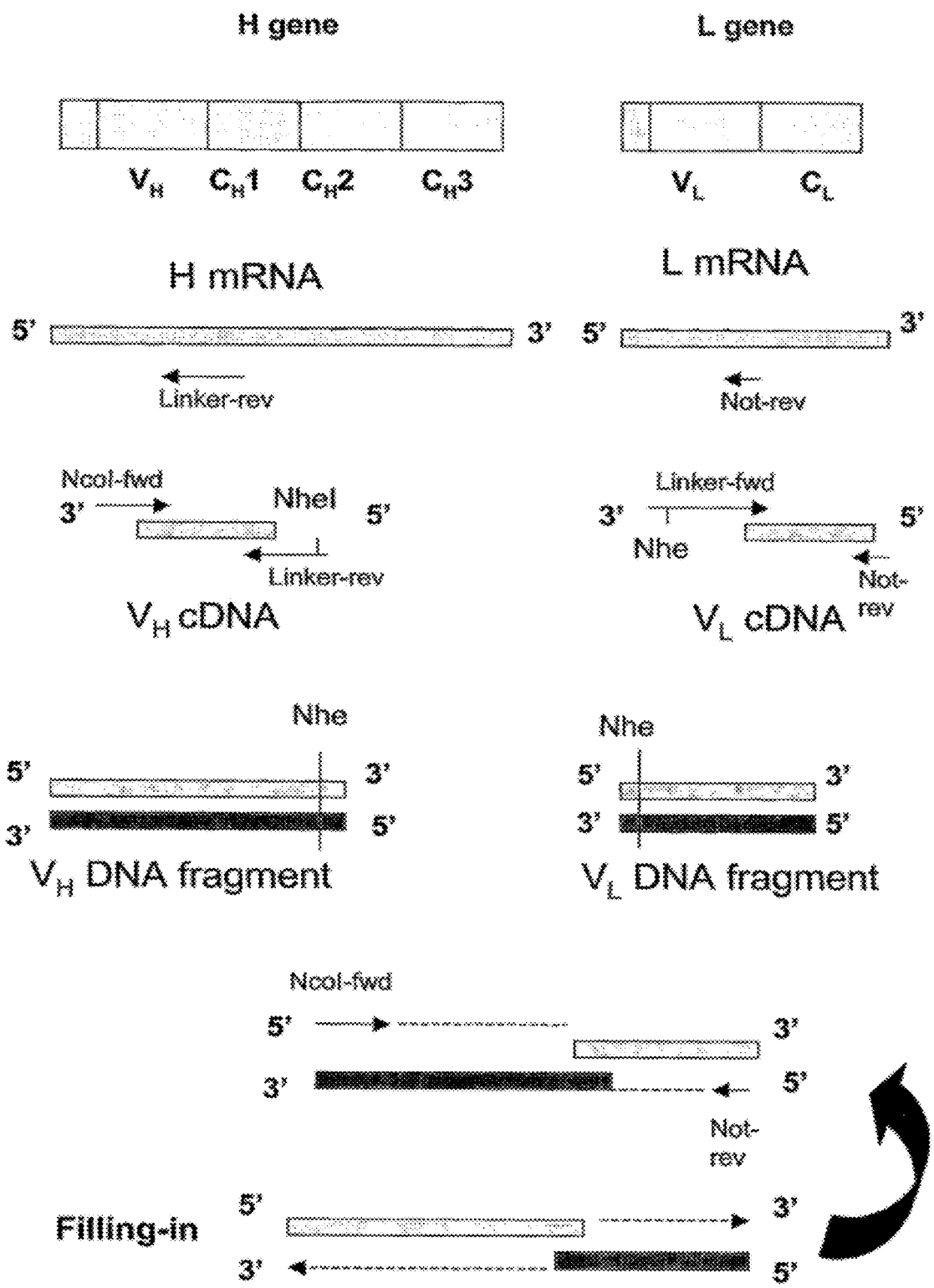
FIG. 2 is a schematic diagram of an outline of the procedure for heavy (H) and light (L) chain synthesis and their connection with the linker sequence.

Primers that can be used to amplify mouse antibody variable heavy and light chains as well as primers to connect these chains by a peptide linker and primers to amplify the assembled antibodies were generated. These primers were used to generate a scFv library from the spleens of immunized mice and from hybridoma 196 that expressed anti-Aβ antibody. Novel scFv antibodies were isolated from these sources and designated as RCK37 and RCK22, respectively. These antibodies when displayed on filamentous phage or as a soluble protein molecule, stabilized by the maltose binding protein, can prevent the fibrilization of Aβp 1-40 and can disaggregate Aβp 1-40 fibrils generated in vitro. They also stained amyloid neuritic plaques on slices of transgenic mice. Single domain antibodies with only the heavy or light chain of RCK37 were generated and were also shown to prevent the fibrilization of Aβp 1-40 and can disaggregate Aβp fibrils generated in vivo.

The present invention provides an antibody against the β-amyloid peptide. The anti-Aβp antibody according to the present invention contains the complementarity-determining regions (CDRs) of an antibody heavy chain or light chain, where the CDRs are the hypervariable regions of an antibody or immunoglobulin molecule that recognize and bind an epitope. The CDRs contained by the anti-Aβp antibody according to the present invention are a combination of CDR1, CDR2, and CDR3 sequences selected from: (1) SEQ ID NOs:10, 12 and 14 (heavy chain CDRs of RCK37); (2) SEQ ID NOs: 16, 18 and 20 (light chain CDRs of RCK37); (3) SEQ ID NOs: 22, 24 and 26 (heavy chain CDRs of RCK22); and (4) SEQ ID NOs: 28, 30 and 32 (light chain CDRs of RCK22).

Preferably, the anti-Aβp antibody of the present invention is a single chain (scFv) antibody or a single domain (heavy or light chain of Fv) antibody. When the antibody is a single domain antibody, it has the combination of CDR sequences of (1), (2), (3) or (4) above and when the antibody is a scFv antibody, it has the combination of CDR sequences of (1) plus (2) or (3) plus (4). Most preferably, the single chain scFv antibody according to the present invention has the amino acid sequence of either SEQ ID NO:6 (RCK37) or SEQ ID NO:8 (RCK22) and the single domain antibody according to the present invention has the amino acid sequence corresponding to residues 1 to 124 or residues 140 to 247 of SEQ ID NO:6.

The present invention is also directed to a nucleic acid molecule which encodes the anti-Aβp antibody of the present invention. Preferably, the nucleic acid molecule includes the nucleotide sequence of either SEQ ID NO:5 or SEQ ID NO:7 when the nucleic acid molecule encodes a single chain scFv antibody or includes nucleotides 1 to 372 or 418 to 741 of SEQ ID NO:5 when the nucleic acid molecule encodes a single domain antibody.

The present invention further provides a vector which contains the nucleic acid molecule encoding the anti-Aβp antibody of the present invention, preferably as an expression vector capable of expressing the anti-Aβp antibody in a host cell.

Further aspects of the present invention include a host cell transformed with the vector of the present invention and a method for producing and isolating the anti-Aβp antibody of the present invention. This method of production involves culturing the transformed host cell to express and produce an anti-Aβp antibody and then isolating the produced anti-Aβp antibody from the cell culture.

A composition, preferably a pharmaceutical composition which contains an effective amount of the anti-Aβp antibody of the present invention and a pharmaceutically acceptable carrier, diluent, excipient or auxiliary agent, is also provided by the present invention.

Finally, the present invention also further provides a method for inhibiting or treating Alzheimer's disease by administering, preferably intranasally, the anti-Aβp antibody of the present invention by passive immunization to a patient in need thereof to inhibit or treat Alzheimer's disease. Antibodies and methods for passive immunization against Alzheimer's disease and other diseases or disorders characterized by amyloid aggregation are well known in the art. See for example WO 99/27944 and U.S. Pat. No. 5,688,651, the entire contents of each of which are incorporated herein by reference.

Having now generally described the invention, the same will be more readily understood through reference to the following examples which are provided by way of illustration and is not intended to be limiting of the present invention.

EXAMPLE 1

ScFv Antibodies Against β-Amyloid Peptide

In the study in this example, mice were immunized with MAP-(EFRH)$_2$ and an ScFv library displayed on filamentous phage. MAP is an abbreviation for the multiple antigen peptide presentation disclosed in WO 2003/076455. Anti-EFRH antibodies were selected by biopanning. Also, a single chain antibody was generated from Hybridoma 196 that express antibodies against EFRH (SEQ ID NO:33). The best binding ScFv antibodies were either displayed on filamentous phage or produced as soluble MBP (maltose binding site)-fused antibodies and used for further investigation.

Materials and Methods mRNA Extraction

Mice were immunized with MAP-EFRH$_2$ and developed high titer of antibodies to the EFRH (SEQ ID NO:3) epitope. The spleens of 5 mice were excised, cut into small pieces and homogenized in RNA extraction reagent (tri-reagent, Biological Industries, Kibbutz Mishmar Haemek, Israel). RNA was extracted according to the manufacturer's instructions, precipitated and suspended in dH$_2$O. mRNA was extracted using μMacs mRNA isolation kit (Miltenyi Biotec, Bergisch Gladbach, Germany).

RNA and mRNA were also extracted from hybridoma cells that expressed monoclonal antibodies against the EFRH (SEQ ID NO:33) epitope using the same procedures as above.

Primer Design

Mouse variable heavy and light chains sequence-alignments were used from the interface of the Kabat data bank (kabatdatabase.com) and the Antibody Group (ibt.unam.mx/vir). Degenerated primers were designed according to consensus amino acids in the amino- and carboxy-termini of the variable heavy and light chains (Table 1). The sequences of the forward and reverse primers of the heavy and light chains were used to design the other primers. Linker primers to join the heavy and light chains were designed with an NheI site. The linker-rev primer contains at its 5' end about half of the peptide-linker-encoding sequence while the second half-linker sequence is contained in primer linker-fwd. The two primers overlap at 24 nucleotides out of the 48 nucleotides that encode the linker peptide (FIG. 1). Primer NcoI-fwd contains at its 5' an NcoI restriction site and degenerated sequence of the 5' end of the heavy chain. Primer NotI-rev contains the sequence for NotI nuclease and the degenerated sequence of the 3' end of the light chain.

TABLE 1

Library primers

| VH-fwd (23 mer) | (SEQ ID NO: 34) |
|---|---|
| 5'- SANRTBMARYTKSWGSAGYCWGG-3' | |

TABLE 1-continued

Library primers

```
VH-rev 24 mer                                            (SEQ ID NO: 35)
5'-TGMRGAGACNGTGASHRDVGTBCC-3'

VK-fwd 23 mer                                            (SEQ ID NO: 36)
5'-GANRTYKTGMTSACVCARDCTMC-3'

VK-rev 24 mer                                            (SEQ ID NO: 37)
5'-MCGWTTBAKYTCCARSTTKGTSCC-3'

Linker primer-fwd (47 mer)                               (SEQ ID NO: 1)
5'-TCAGGGGGAGGT GCTAGC GGTGGCGGAGGCTCTGAIRTYKTGMTSACICA-3'

Linker primer-rev (47 mer)                               (SEQ ID NO: 2)
5'-GCCACC GCTAGC ACCTCCCCCTGATCCGCCTCCACCTGMRGAGACIGTGASIRIIGT-3'

NcoI primer (fwd) (30 mer)                               (SEQ ID NO: 38)
5'-CATGCCATGGCTSANRTBMARYTKSWGSAG-3'

NoII primer (rev) (33 mer)                               (SEQ ID NO: 39)
5'-ATAGAATGCGGCCGCMCGWTTBAKYTCCARSTT-3'
```

Glossary
B = C or G or T
D = A or G or T
H = A or C or T
K = G or T
M = A or C
N = A or C or G or T
R = A or G
S = C or G
V = A or C or G
W = A or T
Y = C or T
I = inosine Library Construction All the procedures described below have been carried out separately with spleen mRNA and with hybridoma mRNA. Synthesis of the first strand cDNAs of the heavy and light chains variable domains were carried out with primers linker-rev and Not-rev, respectively, using RevertAid synthesis kit (Fermentas, Vilnius, Lithuania) (see procedure outline in FIG. 2). Primer NcoI-fwd was added to the $V_H$ reaction and primer Linker-fwd was added to the $V_K$ reaction. Amplification of the heavy and light chains, each with an extended linker-half was carried out using AmpliTaq DNA polymerase (Perkin Elmer). The heavy and light chains were gel purified and digested with NheI followed by digestion of $V_H$ fragments with NcoI and $V_K$ fragments with NotI (these two sites are contained in the 5' region of primers NcoI-fwd and NotI-rev, respectively). For the spleen library, 0.8 µg of each of the digested chains were combined with 1 µg pCANTAB5E (Amersham BioSciences, Piscataway, N.J.) vector that was modified to contain an NcoI site and was linearized by NcoI and NotI digestion. For the hybridoma library, 50 ng of each fragment and vector were ligated. Tri-partite ligations were performed using T4 DNA ligase for 2 hr at room temperature. The ligated mixtures were transferred into E. coli TG1 cells by electroporation. Transformants were selected on 2YT agar plates with 100 µg/ml carbenicillin for 12 hr at 30° C. The colonies were scraped with disposable scrapers and suspended in 2YT liquid medium supplemented with 100 µg/ml carbenicillin. The slurries were divided to aliquots and kept at −75° C. Two libraries were constructed, one from the spleen mRNA and one much smaller from hybridoma mRNA.

Biopanning 25 cm² flasks were coated with 20 µg/ml avidin (Sigma) in 0.1M NaHCO₃, pH 9.0, overnight at 4° C. A biotinylated peptide composed of amino acids 1-16 of the Aβ peptide at 1 µg/ml was applied to the coated flasks followed by blocking with 10% milk powder in PBS at room temperature.

Phages were prepared from each library by diluting 50 µl aliquots into 10 ml 2YT with 100 µg/ml carbenicillin and 0.2% glucose. Bacteria were grown to late-log phase and infected with 1×10¹⁰ cfu of helper phage M13K07 (New England Biolabs, Beverly, Mass.), for 30 minutes at 37° C. The infected bacteria were centrifuged and the supernatant which contained non-infected phages was discarded. The cells were suspended in fresh 2YT with 100 µg/ml Carbenicillin, 50 µg/ml Kanamycin and 0.2 mM IPTG, and grown over night at 37° C. Phages were extracted as described elsewhere, precipitated with PEG-NaCl and suspended in 2 ml PBS and 5% blocker. Phages were applied to the previously blocked flasks and allowed to bind the peptide for 2 hrs at 37° C. Flasks were stringently washed with PBST (0.1%-1% TWEEN 20) and PBS. Late-log-phase growing TG1 cells were added and allowed to be infected with phages that bound the antigen. Aliquotes of the infected bacteria were diluted and plated on carbenicillin plates to estimate the titer of bound phage, and the rest of bacteria were used for further biopanning rounds.

Individual colonies that grew on selection plates were used to produce phages that were retested for antigen binding (by ELISA). Positive clones were kept for further analysis and as possible candidates for vaccine application and soluble protein production.

ELISA

Phages produced from individual bacteria were tested for their ability to bind either the biotinylated 1-16 peptide or beta amyloid peptide 1-40. Wells of microtiter plates (Maxisorb, Nunc) were coated with 20 µg/ml avidin (Sigma) in 0.1 M NaHCO₃ pH 9.0 over-night at 4° C.

The wells were blocked with 5% milk powder in PBS for 1 hr at 37° C. Phages displaying ScFv candidates were diluted to $10^{12}$/ml in 1% blocking solution and applied to the wells for 1 hr at 37° C. The wells were washed 3 times with PBST (0.05% TWEEN 20) and 3 times with PBS. Mouse anti-phage antibodies were applied at 1 µg/ml followed by a secondary anti-mouse horse-radish peroxidase (HRP)-conjugated antibody. HRP activity was detected at room temperature for 20 minutes using Ortophenylenediamine (OPD) reagent and measured at 492 nm with reference reading at 405 nm. Helper phage was used as a negative control and anti beta-amyloid-peptide antibody for positive control. For testing the binding of candidate phages to beta amyloid peptide, soluble Aβ 1-40 (Sigma) was diluted to 10 µg/ml in sterile $dH_2O$ and 50 µl aliquotes were distributed in microtiter plates and incubated over night at 37° C. The next day, the plates were washed, blocked and the detection of positive clones was carried out as described above.

Immunostaining

Phages displaying positive ScFvs were used to stain paraffin embedded brain sections of hAPP transgenic mice that contained amyloid plaques. Phages were diluted to $10^{12}$/ml in PBS and were overlaid on sections that were previously blocked with Histamouse (Zymed/Invitrogen, Carlsbad, Calif.). Mouse anti-phage antibodies were added at a concentration of 0.1 µg/ml and polymer (Zymed/Invitrogen) was used as a detecting tool. HRP reaction was develop using DAB. The sections were visualized for plaque staining using Leica DMLB microscope and Images were photographed with a ProGress C14 color video camera.

Soluble ScFv Constructs and Purification

Selected scFvs were removed by NcoI and NotI digestion and cloned in pMAL vector (New England Biolabs) that was modified to include an NcoI site in its multiple cloning site (MCS). This translational fusion caused the cloned scFvs to form a single protein with the maltose binding protein at their N termini. The plasmids were transformed into E. coli strain BL21-trxB. Single colonies were grown in 100 ml 2YT supplemented with 100 µg/ml carbenicillin and 1% glucose, to mid-log phase (OD 0.5 at 600 nm). IPTG at 1 mM final concentration was added and the cells kept growing for 3 hr at 32° C. The cells were harvested and suspended in column buffer (20 mM Tris-HCl, pH 7.4; 200 mM NaCl; 1 mM EDTA) with Complete Mini EDTA free (protease inhibitor) (Roche). They were sonicated and centrifuged. The supernatant was collected and filtered through 0.45 mm filter. The crude extract was loaded on manually packed amylose column and protein chromatography was carried out using Akta Prime (Amersham Biosciences). MBP-fused scFvs and MBP alone were eluted into fraction collector using elution buffer (column buffer plus 0.3 mM maltose).

Results

Positive Phage-ScFv Selection

Figure 4:
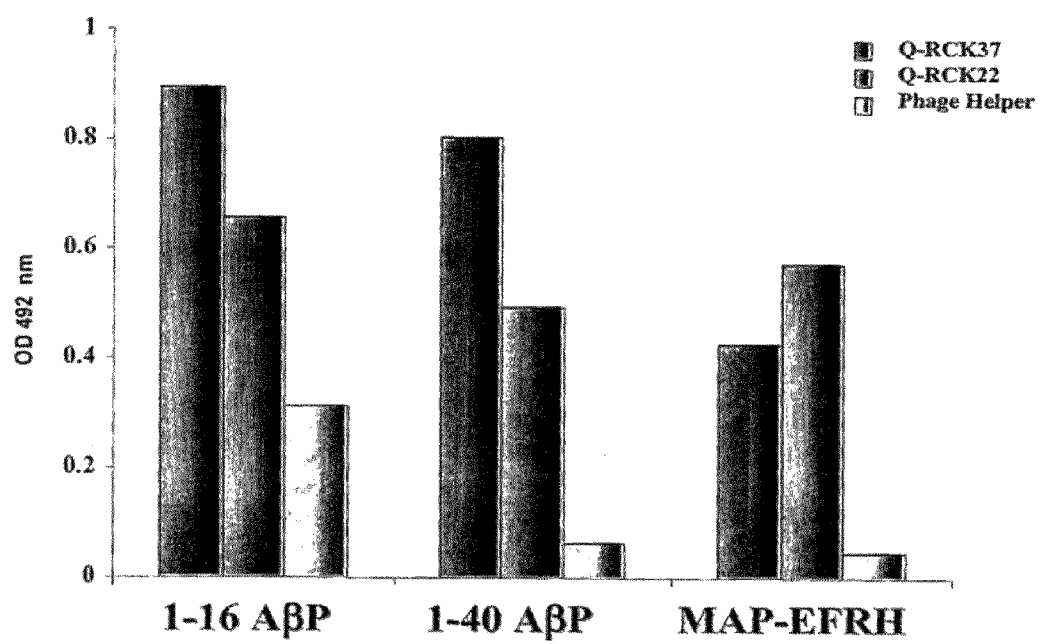
FIG. 4 is a graph of the results of an ELISA assay demonstrating the binding of Q-RCK37, Q-RCK22 and Q-helper to three different antigens which all harbor the EFRH (SEQ ID NO:33) epitope. The results are depicted as OD measurements at 492 nm.

The spleen ScFv library contained an estimated number of $5\times10^5$ clones, about 6% of which were self-ligated vector. Four rounds of biopanning were performed. The first round started with an approximate number of $3\times10^{12}$ phages and ended with a calculated number of 485,000 cfu (based on plating of diluted bacteria). At each additional panning cycle the phage titer was about 10 fold lower and 270 Colonies from each panning cycle were examined by ELISA and candidates that showed high absorbance at 492 nm (>0.1 OD), compared to helper phage control (0.003-0.005 OD), were analyzed by PCR using primers S1 and S6 of pCANTAB5E. Candidates which contained full length ScFv fragment were also digested with NheI to verify correct assembly of the heavy and light chains. A total of thirty final candidates were sequenced. The best clone was designated Q-RCK37 and used in immunostaining of Aβ plaques. The hybridoma library contained a few thousand clones. One cycle of panning was performed and 30 colonies were digested and divided into 2 groups. One group consisted of 28 identical clones and the other group of 2 identical clones. The latter differ in a small insertion in the light chain. One out of the 28 identical clones was designated Q-RCK22. The nucleotide and amino acid sequences of RCK37 and RCK22 as well as their CDR sequences are shown in FIGS. 3A-3D. An ELISA analysis that compares its binding together with Q-RCK37 and helper phage as a control is shown in FIG. 4.

Immunohistology

Figure 5A:
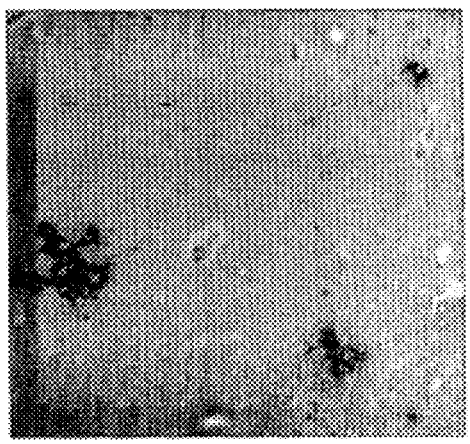
FIGS. 5A-5C show amyloid plaque stained brain sections of hAPP tg mice where
Figure 5B:
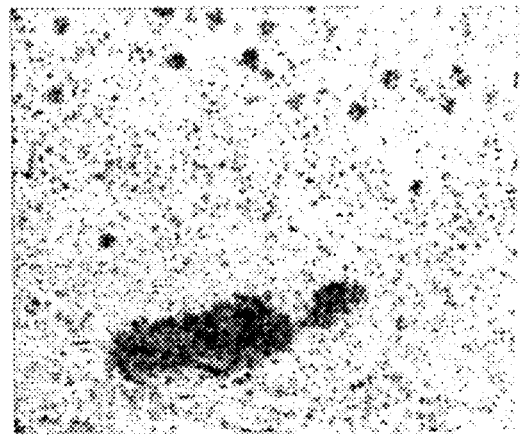
Figure 5C:
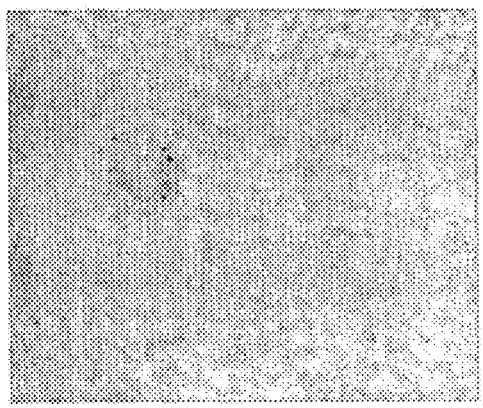

Phages Q-RCK37, Q-RCK22 and helper phage as a control, were used to stain plaques of transgenic mice that express mutation V717F in APP and the Swedish mutation in the β-secretase cleavage site on APP. These mice develop a high number of plaques in their brains. Q-RCK22 stained mostly plaques. Q-RCK37 stained plaques and what is suspected to be neurofibrillary tangles. Most of the staining occurred in the cortex section of the brain (FIGS. 5A-5C).

Soluble ScFv

Figure 6:
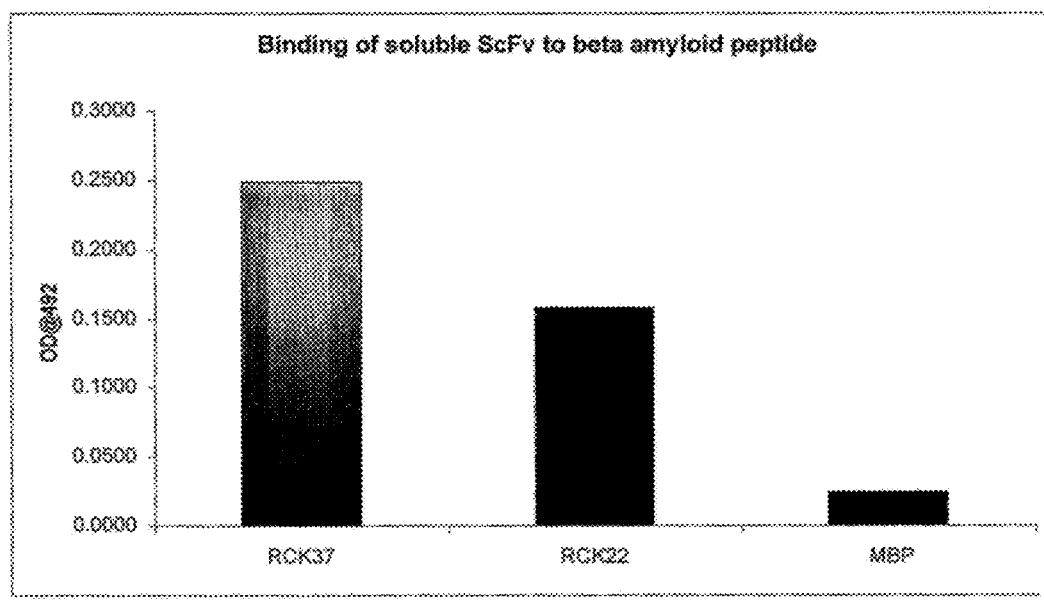
FIG. 6 is a graph of the results of an ELISA assay demonstrating the binding of soluble MBP-ScFv to β-amyloid peptide and the binding of MBP alone as a control.

Previous studies demonstrated that the maltose binding protein stabilizes foreign proteins when expressed in E. coli and helps them to maintain being soluble in the bacterial cytoplasm (Bach et al., 2001). RCK37 and RCK22 were fused to the MBP gene and expressed in E. coli BL21-trxB strain which possesses a thioredoxin-reductase mutation. This strain of bacteria facilitates cytoplasmic disulfide-bond formation which increases the fraction of properly folded protein. Following expression of RCK37 and RCK22, RCK37 and RCK22 were purified by affinity chromatography on amylose resin and were tested by ELISA for binding to APP. Both soluble ScFvs bound AβP were compared to MBP alone, which served as a control (FIG. 6).

EXAMPLE 2

Single Domain Antibodies Against β-Amyloid Peptide

In order to minimize the size of scFv37 antibody, the heavy and light chains of scFv were cloned separately in a pET28 vector and each molecule was expressed in an E. coli BL21 lysS strain. The proteins were extracted from inclusion bodies and checked by ELISA for the binding of AβP (1-40) that was preaggregated overnight, and also for the binding of amino acids 1-16 of AβP.

Materials and Methods

Cloning

The heavy and light chain of RCK37 were synthesized and amplified by PCR using the following primers in Table 2 below:

TABLE 2

| HEAVY CHAIN | |
|---|---|
| 37H-fwd:<br>5'- CATATGGCTCATGTCCAG-3' | (SEQ ID NO: 40) |
| 37h-REV:<br>5'- CTCGAGTGCAGAGACGGTGAC-3' | (SEQ ID NO: 41) |
| LIGHT CHAIN | |
| 37L-fwd:<br>5'-CATATGGAGATAATGATAACGCAG-3' | (SEQ ID NO: 42) |
| 37L -rev:<br>5'-CTCGAGGCGTTTCATCTCCAG-3' | (SEQ ID NO: 43) |

PCR was carried out with Qiagen enzyme and a scFv37-carrying plasmid as a template DNA, using the following protocol: initial denaturation, 2 min at 94° C., followed by 25 cycles of 30 sec denaturation at 94° C., annealing for 45 sec at 48° C.; and 1 min DNA synthesis at 72° C. The final products contained the net nucleotide sequence of the heavy and light chains of RCK37. The PCR fragments were cloned in pGEM-T vector (Promega, Madison, Wis.), and the fragments were excised by NdeI and XhoI digestion and cloned in pET28 vector (Novagen, Madison, Wis.) in which the BglII-XhoI fragment was exchanged with the same fragment from pET21. This exchange enables the heavy or light chains to be fused to the His tag at the C-terminus only. The resulting ligated DNA molecules were transferred to *E. coli* strain BL21 lysS (Novagen). For heavy or light chain production, cells were grown in 1 liter culture at 37° C. to late-mid log phase (OD600=0.6). IPTG induction was started at this stage, using 0.8 mM IPTG overnight at 30° C. The next day, cells were centrifuged, and inclusion bodies were prepared as described in Biotechniques, Vol XI, No. 6, December 1991, pp 748-752. The purified heavy and light chains were dialyzed overnight in PBS to exchange the renaturation buffer in which they were suspended in the last step of inclusion body extraction. Protein concentrations were determined and the binding of the heavy and light chains to Aβp 1-40 was determined by ELISA.

ELISA

β-amyloid peptide 1-40, at increasing concentrations (0-5 µM) was applied to 96 well plate in duplicates of 50 µl each and incubated in 37° C. overnight. Wells were washed and blocked with 3% milk powder in PBS for 1 hr at 37° C. The 37H or 37L molecules were applied at the constant concentration of 12.5 µM, and 1 OD5 (monoclonal antibody against the N terminus of Aβ peptide) was also applied as a control at 1 µg/ml, for 1 hr at 37° C. Detection of 37H or 37L was carried out with mouse anti-H is antibody and with anti-mouse antibody for 1 OD5, followed by Goat-anti mouse antibody conjugated to HRP (horse radish peroxidase) for all three antibodies. In another assay, a constant concentration of 10 µM β-amyloid peptide 1-40 was applied to 96 well plate and the 37H or 37L molecules were applied at different concentrations (from 3.125 µM to 25 µM). The rest of the ELISA assay was performed as described above.

ThT

In vitro fibril formation of Aβp was measured by the Thioflavin T (ThT) binding assay. ThT binds amyloid fibrils and exhibits enhanced fluorescence emission at 485 nm upon excitation at 435 nm. Fluorescence intensity is correlated with the degree of Aβp fibril formation. Aβp was solubilized in $dH_2O$ (pH 5.5) to 23.2 µM, aliquoted into 20 µl samples in blocked tubes and incubated in a 37° C. humidified incubator for a week. For disaggregation assay, 20 µl aliquote of 12.5 µM 37H, 25 µM 37H or 1 µM mAb 1 OD5 were added at this point to the Aβp aliquots, mixed well and incubated together for an additional week. To measure fluorescence as a measure of the amount of fibrils, 0.98 ml aliquots of 2 µM ThT (in 50 mM glycine, pH 9.0) were added to 20 µl Aβp preparations and read in an LSB-50 Perkin Elmer spectorofluorimeter.

Results

Figure 7A:
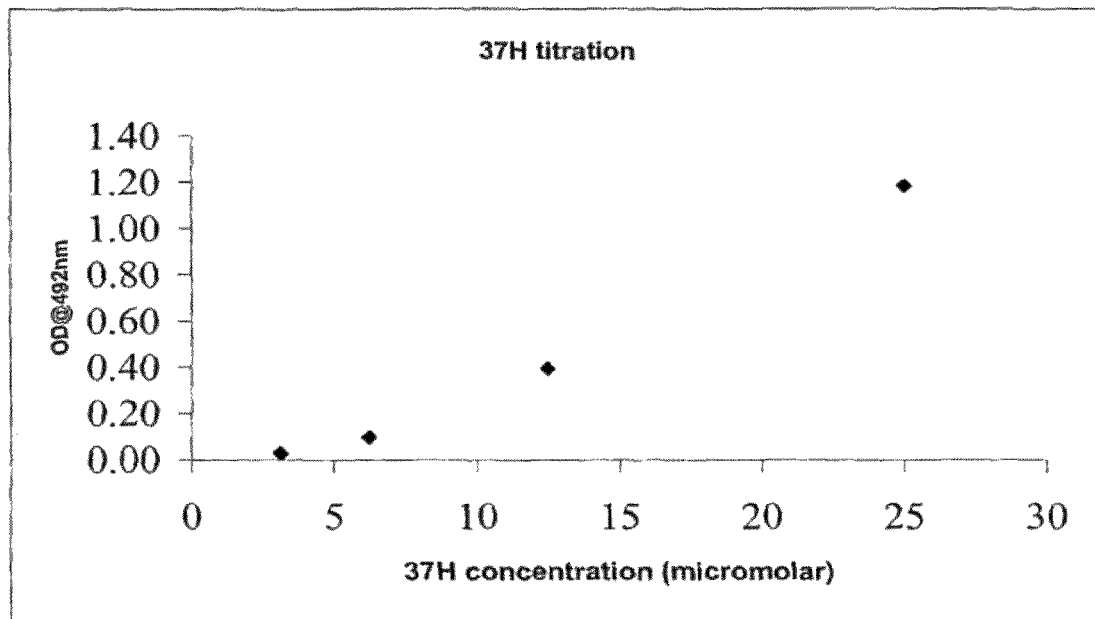
FIGS. 7A-7D are graphs showing the results of the ELISA assay performed with constant β-amyloid concentrations and elevated 37H or 37L concentrations. The binding of different concentrations of 37H (FIG. 7A) and 37L (FIG. 7B) to 10 μM Aβp 1-40 and the binding of the 12.5 μM 37H (FIG. 7C) and 37L (FIG. 7D) to different concentrations of Aβp 1-40 are shown.
Figure 7B:
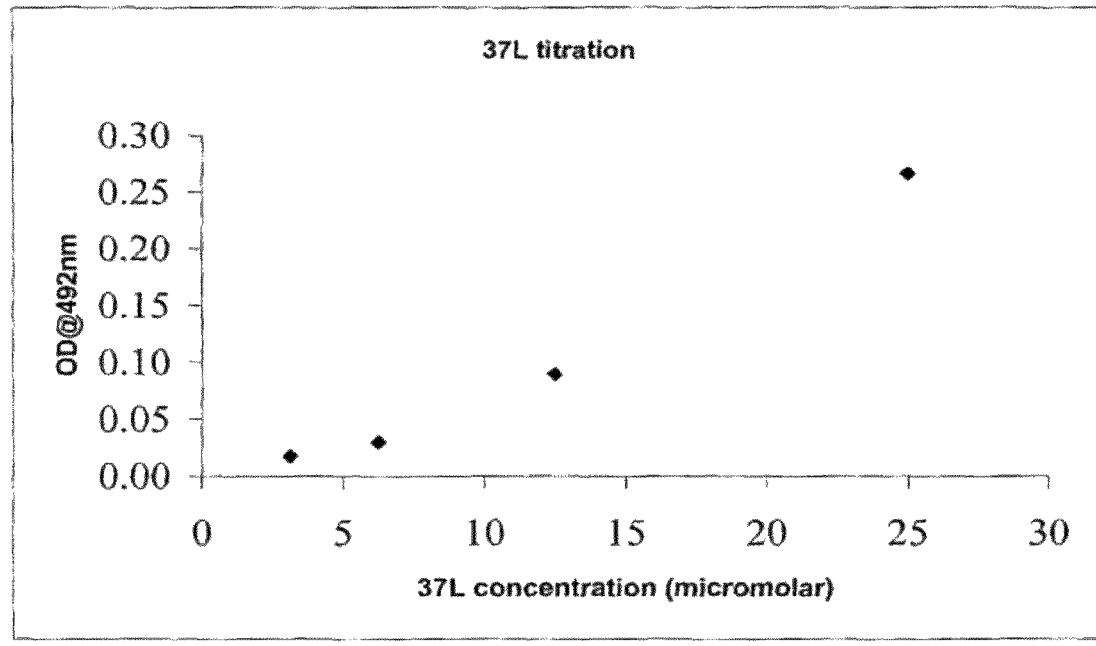

FIGS. 7A and 7B show the results of the ELISA assay performed with constant β-amyloid concentrations and elevated 37H or 37L concentrations. It demonstrates that both 37H and 37L bind Aβp 1-40 (Abeta 1-40), however the binding of 37H is 5 times stronger than the binding of 37L. The binding is linear at the concentrations examined, suggesting a real affinity of the antibody to β-amyloid peptide. The 10 mM β-amyloid peptide used was high enough to bind even the highest antibodies concentration used.

Figure 7C:
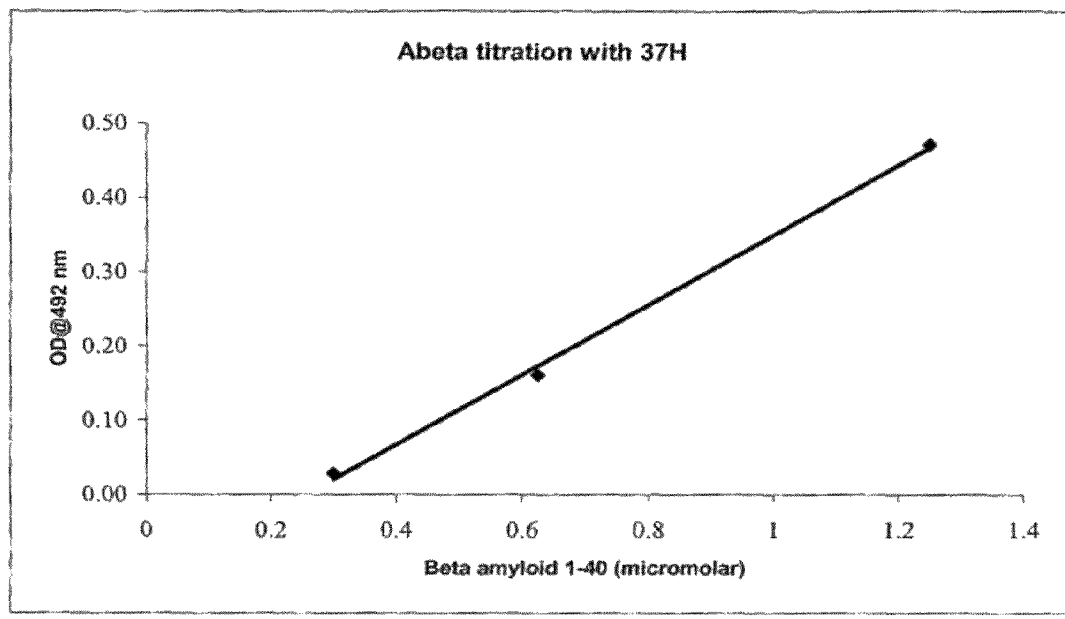
Figure 7D:
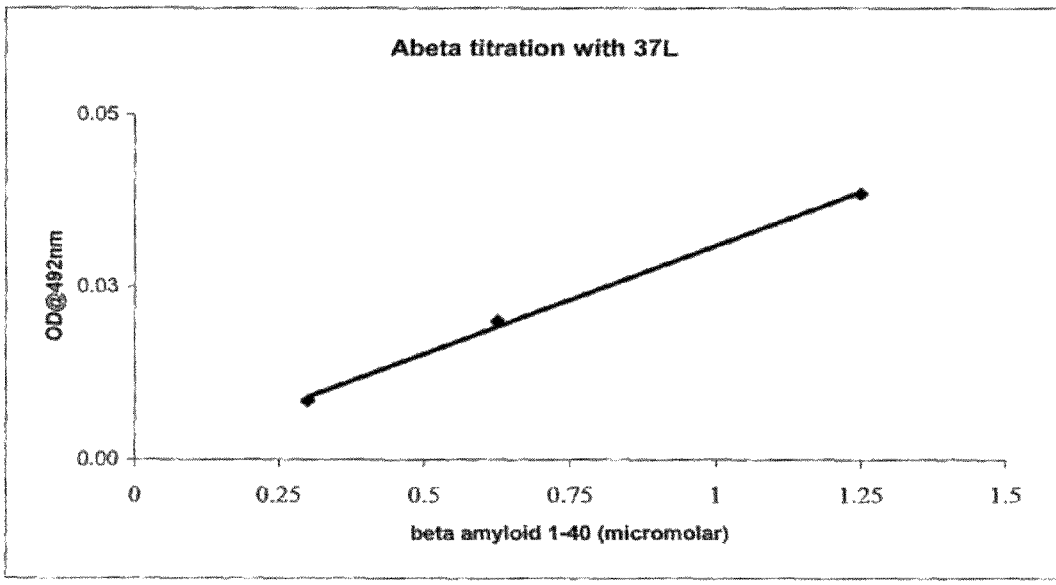

The same linear reactivity is observed when the concentrations of the antibodies are constant (12.5 µM), while the antigen's concentrations are titrated (FIGS. 7C and 7D); however, in this case, the binding is linear only up to 1.25 µM Aβp. In the two other concentrations examined, 2.5 and 5 µM, the binding was slightly lower (not shown), suggesting that the β-amyloid above 1.25 µM is aggregated and the binding is reduced as a result. This probably happened also in the assay presented in FIGS. 7A and 7B, but because 10 µM Aβ were used, there were enough linear β-amyloid molecules to bind the antibodies that were applied. The binding of antibody 1 OD5 is not shown in FIGS. 7A-7D.

Figure 8A:
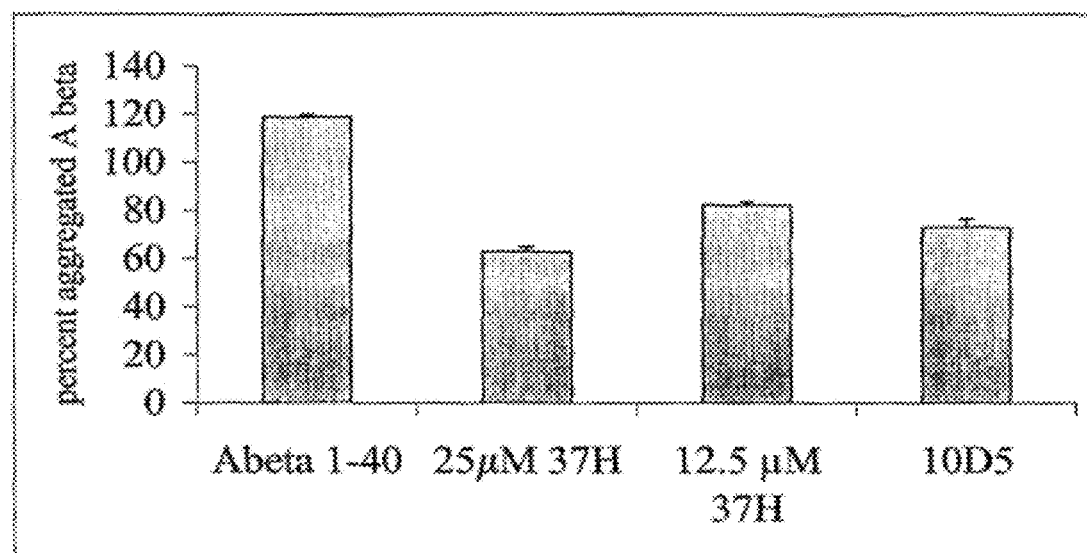
FIGS. 8A and 8B show the binding of 37H to β-amyloid fibrils in solution and their partial disaggregation.
Figure 8B:
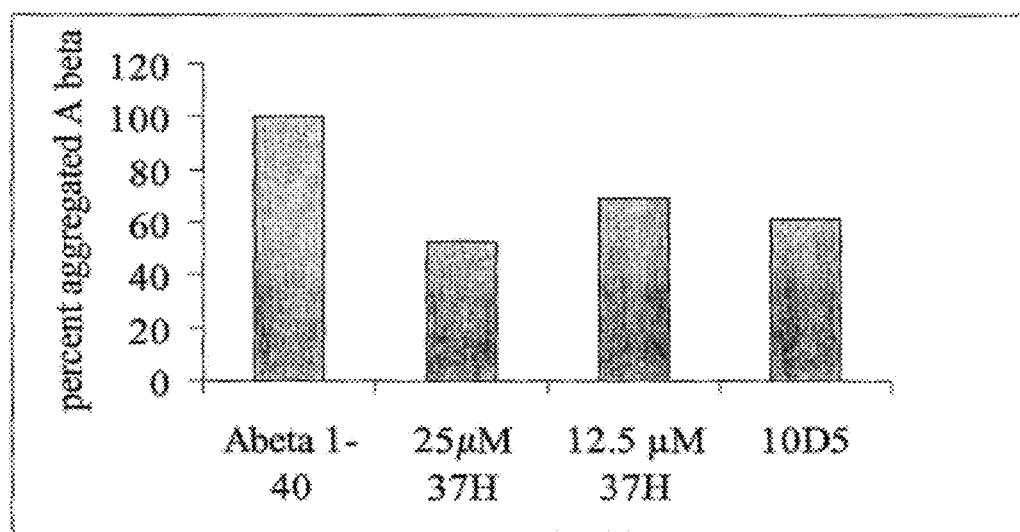

In FIGS. 8A and 8B, the binding of 37H to β-amyloid fibrils in solution and their partial disaggregation is shown. Compared to the monoclonal antibody 1 OD5, the concentrations needed to solubilized the Aβ fibrils are relatively higher, but producing 37H is much easier and economical. Table 3 below provides a summary of the relevant aggregation values and the values of disaggregation.

TABLE 3

|  | Percent Aggregation | Percent Disaggregation |
|---|---|---|
| A beta only | 100 | 0 |
| Plus 25 µM 37H | 52.95 | 47.04459 |
| Plus 12.5 µM 37H | 62.29 | 30.71043 |
| Plus 1 µM 10D5 | 61.35848357 | 38.64152 |

EXAMPLE 3

In Vivo Experiments

Material and Methods

TAPIR assay with nanobody 37H

Soluble nanobody 37H (single domain antibody) was used to stain brain sections of a PDAPP transgenic mice. Paraffin sections (5 µm) were deparaffinized by a series of xylenes, hydrated with a gradient series of ethanol, and quenched by 3% $H_2O_2$ in methanol and then blocked with Histamouse kit blocker A (Zymed, USA). 37H protein was diluted to 10 µg/ml PBS and overlaid on the sections for 2 hr at room temperature. Mouse anti-His tag-HRP conjugated antibodies were added at a concentration of 0.1 mg/ml. Slides were developed with DAB (Zymed).

Animals

Male and female PDAPP mice and non-Tg littermates were used. The mice were genetically engineered by employing a platelet-derived growth factor promoter driving a hβAPP minigene encoding the $717_{V-F}$ mutation associated with familial AD. The ambient temperature was maintained at 25° C.±1 and a 12:12-h light-dark cycle was maintained throughout the experiment. Food and water were available ad libitum. Animal care, maintenance and experimental procedures were according to the National Institutes of Health Guide for the Care and Use of Laboratory Animals.

Immunization with Phage-Anti EFRH scFv

The administration of scFv-phage to the mice was started when they were nine months old. Each mouse of the scFv-phage group received $10^{11}$ phages per administration every 2 weeks for 2 months and then once a month for a total of 14 applications (administrations). Intranasal administration was done as follows: briefly, the mouse was held firmly with its head pointing to the ceiling, with one hand, and with the other hand, phages were applied using a 100 µl pipette with narrow sterile protected tips that contained 20 µl of solution. Approximately 10 µl per nostril were applied, in short intervals to ensure that the solution wetted the mucosa of the nose. The scFv 22 and scFv 37 treated groups included 12 mice each. The PBS control group included 11 mice.

Phage 37 was also applied by intraperitoneally (IP) method, $10^{11}$ phages in 300 µl were injected into each mouse peritoneum. The number of administrations was similar to the intranasal (IN) treatment. Five mice were included in this group.

Preparation of Brain Tissues

At the end of the experiment, the mice (20 months old) were euthanized, using an overdose of a standard inhalation of anesthesia (Isofluran®, Baxter, USA). Next, their brains were removed and the right hemispheres collected from each mouse were fixed for 24 hr in 4% paraformaldehyde/PBS, transferred to PBS (pH 7.4), and then immersed in 30% sucrose in PBS. When the brains sank, they were frozen in Acetone-dry-ice bath. Serial coronal sections (5 µm), in an anterior-to-posterior direction, 250 µm apart from each other, were prepared in a cryostat for histology. The brain pathology was examined after H&E staining and hemosiderin stainings were performed to detect any vascular hemorrhage.

Quantitative Analysis of Amyloid Plaque Load

Two well-defined coronal sections at the levels of −1.6 and −3.6 from bregma were selected for thioflavin-S staining (which stains dense plaques). Sections were hydrated, and stained first with hematoxylin to quench autofluorescence, and then with 1% thioflavin-S for 3 minutes, followed by immersion in 1% acetic acid for 20 minutes, then washed, cleared, and mounted. Images from these sections were captured by a CCD color video camera (ProgRes C14, Jenoptic, Jena, Germany) attached to a Leica DMLB microscope (Leica, Germany) and analyzed with appropriate software (Leica Qwin, Leica, Germany). The total amyloid dense core load in plaques in the cortex and hippocampus was expressed as the percentage of the area stained with thioflavin-S out of the total area of the these areas in each section.

Staining with 21F12, an anti-Aβ 1-42 antibody

This antibody stains soluble and fibrillar Aβ 1-42. Slides with serial brain sections were washed in TBS and quenched in 3% $H_2O_2$ in methanol for 15 min in room temp, followed by 3 washes in TBS. Denaturation was carried out in 90% formic acid for 30 min. at room temp, followed by 3 washes in TBS. Tissue permeabilization was done by 0.3% Triton in TBS for 20 min at room temp followed by 3 washes in TBS. Blocking was done with UV block (LabVision) for 10 min at room temp and antibody 21F12 was applied at 1:1000 in PBS for 1 hr at 37° C. followed by overnight incubation at 4° C. and 3 washes, 5 min each, in TBS. Supes Picture (Zymed, ready to use) was applied for 20 min at room temp with gentle shaking followed by 4 TBS washes, each for 4 min. Developing was done with DAB (Zymed) for 5 min and stopped with multiple $dH_2O$ washes.

Results

Figure 9:
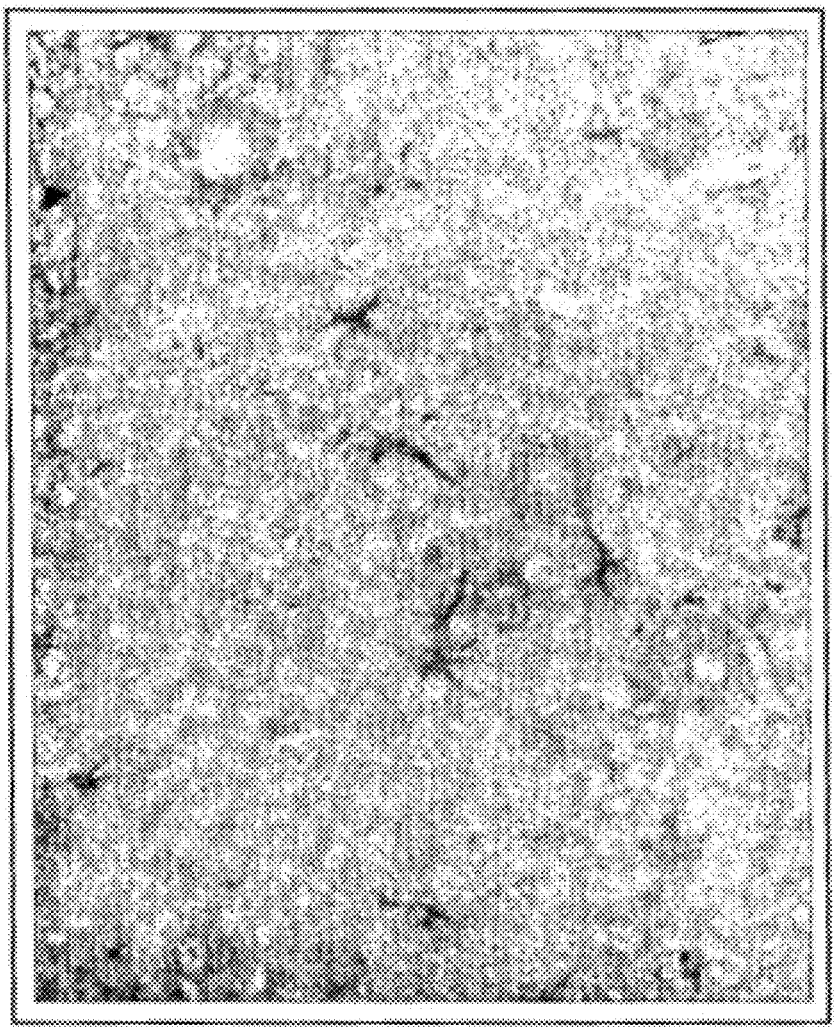
FIG. 9 shows Tapir staining of amyloid plaques in a PDAPP mouse brain section by 37H nanobody.

FIG. 9 shows amyloid plaques of a PDAPP Tg mouse stained with 37H nanobody (the heavy chain of scFv RCK37). Note that the antibody stains plaques, fibrillar and soluble Aβ deposits in the tissue. In heavily condensed plaques, the nanobody stains the outskirts of the plaque that are less condensed. Around some plaques, glial cells that also were stained are visible, probably because they contain beta amyloid deposits.

Figure 10:
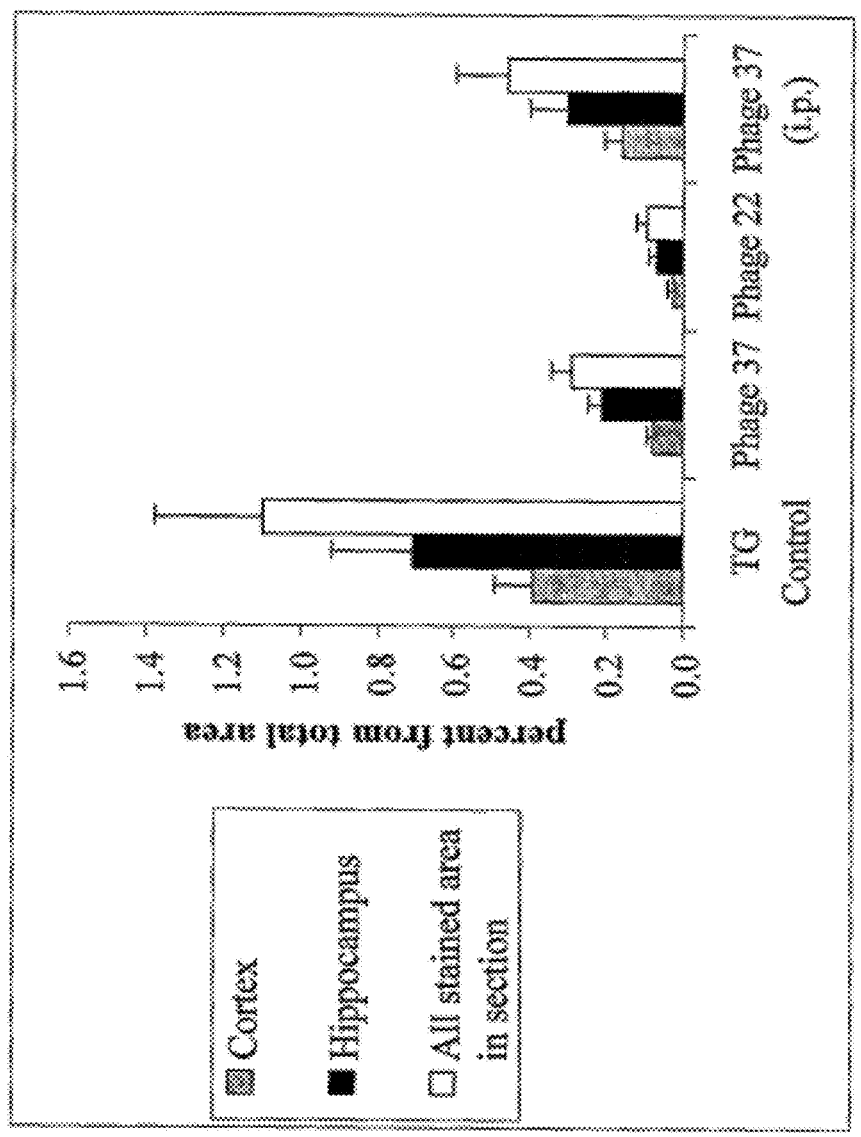
FIG. 10 is a graph showing amyloid load as determined by Thioflavin S staining. Data are presented as the average scores of all mice in each group: n=12 in the scFv treated groups and n=11 in the control group.
Figure 11:
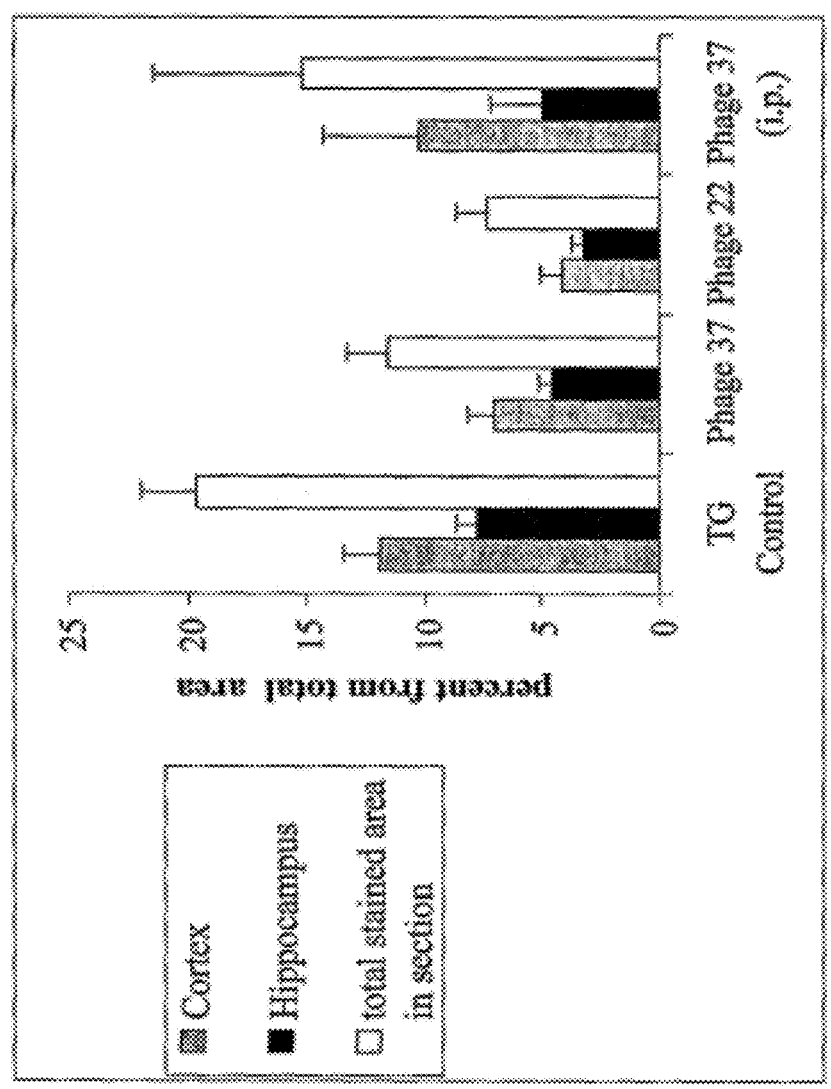
FIG. 11 is a graph showing amyloid load determined by staining with 21F12, an anti-Ab 1-42 antibody. Data are presented as the average scores of all mice in each group: n=12 in the scFv treated groups and n=11 in the control group.

In FIG. 10, a summary of the plaque load detected by thioflavin S staining in the cortex and hippocampus of PDAPP mice treated with phage 22 or phage 37, versus control mice, treated with PBS only, is presented. Phage 37 reduced plaque load significantly in both the cortex and hippocampus areas of mice treated with it by intranasal application. Intraperitoneal (IP) application of phage 37 did not show significant plaque load reduction. Plaque load reduction in phage 22 treated mice was much more dramatic both in the cortex and in the hippocampus, compared to untreated controls.

FIG. 3 shows a summary of the plaque load detected by staining with antibody 21F12 in the cortex and hippocampus of PDAPP mice treated with phage 22 or phage 37, versus control mice, treated with PBS only. Here too, both phage 37 and phage 22 reduced plaque load significantly in both the cortex and hippocampus areas of mice treated with these scFvs by intranasal application. IP application of phage 37 did not show significant plaque load reduction.

Both scFv 22 and scFv 37 significantly reduced the Aβ load in treated mice brains, They affected the soluble and fibrillary amyloid deposits (stained with 21F12 antibody) as well as the dense amyloid plaques (stained by thioflavin S). Furthermore, intranasal administration/application of the phage scFVs is an effective way to introduce the scFv antibodies to the mice brains, compared with the IP application of phage 37. While IP administration of phage did show reduced plaque load, the reduced plaque load was not as significant as by intranasal administration.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

REFERENCES

Bach H, Mazor Y, Shaky S, Shoham-Lev A, Berdichevsky Y, Gutnick D L, Benhar I. *Escherichia coli* maltose-binding protein as a molecular chaperone for recombinant intracellular cytoplasmic single-chain antibodies. *J Mol. Biol.* (2001) 312(1):79-93

Bacskai B J, Kajdasz S T, McLellan M E, Games D, Seubert P, Schenk D, Hyman B T. 3. Non-Fc-mediated mechanisms are involved in clearance of amyloid-beta in vivo by immunotherapy. *J. Neurosci.* 2002 Sep. 15; 22(18):7873

Frenkel, D., Solomon B. and Benhar I. Modulation of Alzheimer's beta amylois neurotoxicity by site-directed single-chain antibody. *J. of Neuroimmunology* (2000) 106:23-31.

Schenk D., Barbour R. Dunn W. et al. Immunization with amyloid-beta attenuates Alzheimer-disease-like pathology in the PDAPP mouse. *Nature* (1999) 400:173-177.

What is claimed is:

1. An antibody against β-amyloid peptide, comprising the antibody heavy chain complementarity-determining regions (CDRs) of SEQ ID Nos: 22, 24 and 26; or the antibody heavy chain and light chain CDRs of SEQ ID Nos: 22, 24, 26 and SEQ ID Nos: 28, 30 and 32.

2. The antibody of claim 1, which is a single domain antibody.

3. The antibody of claim 2, wherein the single domain comprises the CDR sequences of SEQ ID Nos: 22, 24 and 26.

4. The antibody of claim 1, which is a single chain (scFv) antibody.

5. The antibody of claim 4, comprising the CDR sequences of SEQ ID Nos: 22, 24, 26, 28, 30 and 32.

6. The antibody of claim 5, comprising the amino acid sequence of SEQ ID NO:8.

7. A pharmaceutical composition comprising an effective amount of the antibody of claim 1 and a pharmaceutically acceptable carrier, diluent, excipient or auxillary agent.

8. A method for reducing β-amyloid plaque load in the brain, comprising administering the antibody of claim 1 to a patient in need thereof.

9. The method of claim 8, wherein the antibody is administered intranasally.

* * * * *

```
                       SEQUENCE LISTING

<160> NUMBER OF SEQ ID NOS: 43

<210> SEQ ID NO 1
<211> LENGTH: 50
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (36)..(36)
<223> OTHER INFORMATION: n at postion 36 is inosine.
<220> FEATURE:
<221> NAME/KEY: misc_feature
<222> LOCATION: (48)..(48)
<223> OTHER INFORMATION: n at postion 48 is inosine.

<400> SEQUENCE: 1 tcaggggag gtgctagcgg tggcggaggc tctganrtyk tgmtsacnca                 50

<210> SEQ ID NO 2
<211> LENGTH: 57
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (46)..(46)
<223> OTHER INFORMATION: n at postion 46 is inosine.
<220> FEATURE:
<221> NAME/KEY: misc_feature
<222> LOCATION: (52)..(52)
<223> OTHER INFORMATION: n at postion 52 is inosine.
<220> FEATURE:
<221> NAME/KEY: misc_feature
<222> LOCATION: (54)..(55)
<223> OTHER INFORMATION: n at postions 54 and 55 is inosine.

<400> SEQUENCE: 2
gccaccgcta gcacctcccc ctgatccgcc tccacctgmr gagacngtga snrnngt        57

<210> SEQ ID NO 3
<211> LENGTH: 45
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(45)

<400> SEQUENCE: 3 ggt gga ggc gga tca ggg gga ggt gct agc ggt ggc gga ggc tct          45
```

```
Gly Gly Gly Gly Ser Gly Gly Gly Ala Ser Gly Gly Gly Gly Ser
1               5                   10                  15

<210> SEQ ID NO 4
<211> LENGTH: 15
<212> TYPE: PRT
<213> ORGANISM: Artificial
<220> FEATURE:
<223> OTHER INFORMATION: Synthetic Construct

<400> SEQUENCE: 4

Gly Gly Gly Gly Ser Gly Gly Gly Ala Ser Gly Gly Gly Gly Ser
1               5                   10                  15

<210> SEQ ID NO 5
<211> LENGTH: 750
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(750)

<400> SEQUENCE: 5 atg gct cat gtc cag ttt gtg cag tct ggg gga gac tta gtg aag cct        48
Met Ala His Val Gln Phe Val Gln Ser Gly Gly Asp Leu Val Lys Pro
1               5                   10                  15 gga ggg tcc ctg aaa ctc tcc tgt gca gcc tct gga ttc act ttc agt        96
Gly Gly Ser Leu Lys Leu Ser Cys Ala Ala Ser Gly Phe Thr Phe Ser
            20                  25                  30 agc tat ggc atg tct tgg gtt cgc cag act cca gac aag agg ctg gag       144
Ser Tyr Gly Met Ser Trp Val Arg Gln Thr Pro Asp Lys Arg Leu Glu
        35                  40                  45 tgg gtc gca acc att agt agt ggt ggt agt tac acc tac tat cca gac       192
Trp Val Ala Thr Ile Ser Ser Gly Gly Ser Tyr Thr Tyr Tyr Pro Asp
    50                  55                  60 agt gtg aag ggg cga ttc acc atc tcc aga gac aat gcc aag aac acc       240
Ser Val Lys Gly Arg Phe Thr Ile Ser Arg Asp Asn Ala Lys Asn Thr
65                  70                  75                  80 ctg tac ctg caa atg agc agt ctg aag tct gag gac aca gcc atg tat       288
Leu Tyr Leu Gln Met Ser Ser Leu Lys Ser Glu Asp Thr Ala Met Tyr
                85                  90                  95 tac tgt gca aga cat aac tac ggt agt agc tac cct tat gct atg gac       336
Tyr Cys Ala Arg His Asn Tyr Gly Ser Ser Tyr Pro Tyr Ala Met Asp
            100                 105                 110 tac tgg ggt caa gga acc ccc gtc acc gtc tct gca ggt gga ggc gga       384
Tyr Trp Gly Gln Gly Thr Pro Val Thr Val Ser Ala Gly Gly Gly Gly
        115                 120                 125 tca ggg gga ggt gct agc ggt ggc gga ggc tct gag ata atg ata acg       432
Ser Gly Gly Gly Ala Ser Gly Gly Gly Gly Ser Glu Ile Met Ile Thr
    130                 135                 140 cag act cca gta atc atg tct gca ttt tca ggg gag aag gtc acc atg       480
Gln Thr Pro Val Ile Met Ser Ala Phe Ser Gly Glu Lys Val Thr Met
145                 150                 155                 160 acc tgc agt gcc agt tca agt gtt aat tac atg cac tgg tat cag cag       528
Thr Cys Ser Ala Ser Ser Ser Val Asn Tyr Met His Trp Tyr Gln Gln
                165                 170                 175 aag tca ggc act tcc ccc aaa aaa tgg att tat gac aca tcc aaa ttg       576
Lys Ser Gly Thr Ser Pro Lys Lys Trp Ile Tyr Asp Thr Ser Lys Leu
            180                 185                 190 gct tct gga gtc cct gat cgc ttc agt ggc agt ggg tct ggg acc tct       624
Ala Ser Gly Val Pro Asp Arg Phe Ser Gly Ser Gly Ser Gly Thr Ser
        195                 200                 205
```

| | | | | | | | | | | | | | | |
|---|---|---|---|---|---|---|---|---|---|---|---|---|---|---|
| tac | tct | ctc | aca | atc | agc | aga | atg | gag | gct | gaa | gat | gct | gcc | act | tat | 672 |
| Tyr | Ser | Leu | Thr | Ile | Ser | Arg | Met | Glu | Ala | Glu | Asp | Ala | Ala | Thr | Tyr | |
| | | 210 | | | | 215 | | | | 220 | | | | | | |
| tac | tgc | ccg | cag | tgg | agt | agt | aac | cct | ccc | atg | acg | ttc | ggt | gga | ggc | 720 |
| Tyr | Cys | Pro | Gln | Trp | Ser | Ser | Asn | Pro | Pro | Met | Thr | Phe | Gly | Gly | Gly | |
| 225 | | | | | 230 | | | | | 235 | | | | | 240 | |
| aca | aac | ctg | gag | atg | aaa | cgc | gcg | gcc | gca | | | | | | | 750 |
| Thr | Asn | Leu | Glu | Met | Lys | Arg | Ala | Ala | Ala | | | | | | | |
| | | | | 245 | | | | | 250 | | | | | | | |

<210> SEQ ID NO 6
<211> LENGTH: 250
<212> TYPE: PRT
<213> ORGANISM: Artificial
<220> FEATURE:
<223> OTHER INFORMATION: Synthetic Construct

<400> SEQUENCE: 6

Met Ala His Val Gln Phe Val Gln Ser Gly Gly Asp Leu Val Lys Pro
1               5                   10                  15

Gly Gly Ser Leu Lys Leu Ser Cys Ala Ala Ser Gly Phe Thr Phe Ser
            20                  25                  30

Ser Tyr Gly Met Ser Trp Val Arg Gln Thr Pro Asp Lys Arg Leu Glu
        35                  40                  45

Trp Val Ala Thr Ile Ser Ser Gly Gly Ser Tyr Thr Tyr Tyr Pro Asp
    50                  55                  60

Ser Val Lys Gly Arg Phe Thr Ile Ser Arg Asp Asn Ala Lys Asn Thr
65                  70                  75                  80

Leu Tyr Leu Gln Met Ser Ser Leu Lys Ser Glu Asp Thr Ala Met Tyr
                85                  90                  95

Tyr Cys Ala Arg His Asn Tyr Gly Ser Ser Tyr Pro Tyr Ala Met Asp
            100                 105                 110

Tyr Trp Gly Gln Gly Thr Pro Val Thr Val Ser Ala Gly Gly Gly Gly
        115                 120                 125

Ser Gly Gly Gly Ala Ser Gly Gly Gly Ser Glu Ile Met Ile Thr
    130                 135                 140

Gln Thr Pro Val Ile Met Ser Ala Phe Ser Gly Glu Lys Val Thr Met
145                 150                 155                 160

Thr Cys Ser Ala Ser Ser Ser Val Asn Tyr Met His Trp Tyr Gln Gln
                165                 170                 175

Lys Ser Gly Thr Ser Pro Lys Lys Trp Ile Tyr Asp Thr Ser Lys Leu
            180                 185                 190

Ala Ser Gly Val Pro Asp Arg Phe Ser Gly Ser Gly Ser Gly Thr Ser
        195                 200                 205

Tyr Ser Leu Thr Ile Ser Arg Met Glu Ala Glu Asp Ala Ala Thr Tyr
    210                 215                 220

Tyr Cys Pro Gln Trp Ser Ser Asn Pro Pro Met Thr Phe Gly Gly Gly
225                 230                 235                 240

Thr Asn Leu Glu Met Lys Arg Ala Ala Ala
                245                 250

<210> SEQ ID NO 7
<211> LENGTH: 714
<212> TYPE: DNA
<213> ORGANISM: Artificial
<220> FEATURE:
<223> OTHER INFORMATION: Synthetic
<220> FEATURE:
<221> NAME/KEY: CDS

<222> LOCATION: (1)..(714)

<400> SEQUENCE: 7

```
atg gcc cag gtg cag ctg cag cag tct ggg gga ggc tta gtg cag cct      48
Met Ala Gln Val Gln Leu Gln Gln Ser Gly Gly Gly Leu Val Gln Pro
1               5                   10                  15 gga ggg tcc ctg aaa ctc tcc tgt gca gcc tct gga ttc act ttc agt      96
Gly Gly Ser Leu Lys Leu Ser Cys Ala Ala Ser Gly Phe Thr Phe Ser
            20                  25                  30 agg tat ggc atg tct tgg gtt cgc cag act cca gac aag agg ctg gag     144
Arg Tyr Gly Met Ser Trp Val Arg Gln Thr Pro Asp Lys Arg Leu Glu
        35                  40                  45 ttg gtc gca acc att aat agt aat ggc ggt agc acc tat tat cca gac     192
Leu Val Ala Thr Ile Asn Ser Asn Gly Gly Ser Thr Tyr Tyr Pro Asp
    50                  55                  60 agt gtg aag ggc cgt ttc acc atc tcc aga gac aat gcc aag aac acc     240
Ser Val Lys Gly Arg Phe Thr Ile Ser Arg Asp Asn Ala Lys Asn Thr
65                  70                  75                  80 ctg tac ctg caa atg agc agt ctg aag tct gcg gac aca gcc atg tat     288
Leu Tyr Leu Gln Met Ser Ser Leu Lys Ser Ala Asp Thr Ala Met Tyr
                85                  90                  95 ttc tgt gcc aga gga ggt tac ctt gac tac tgg ggc caa ggg acc acg     336
Phe Cys Ala Arg Gly Gly Tyr Leu Asp Tyr Trp Gly Gln Gly Thr Thr
            100                 105                 110 gtc acc gtc tcc tca ggt gga ggc ggt tca gga gga ggt ggc tct ggc     384
Val Thr Val Ser Ser Gly Gly Gly Gly Ser Gly Gly Gly Gly Ser Gly
        115                 120                 125 ggt ggc gga gcg gac atc gag ctc act cag tct cca tct ctg gga gaa     432
Gly Gly Gly Ala Asp Ile Glu Leu Thr Gln Ser Pro Ser Leu Gly Glu
    130                 135                 140 agt gtc acc atc aca tgc ctg gca agt cag acc att ggt aca tgg tta     480
Ser Val Thr Ile Thr Cys Leu Ala Ser Gln Thr Ile Gly Thr Trp Leu
145                 150                 155                 160 gca tgg ttt cag cag aaa cca ggg aaa tct cct cag ctc ctg att tat     528
Ala Trp Phe Gln Gln Lys Pro Gly Lys Ser Pro Gln Leu Leu Ile Tyr
                165                 170                 175 gct gca acc agc ttg gca gat ggg gtc cca tca agg ttc agt ggt agt     576
Ala Ala Thr Ser Leu Ala Asp Gly Val Pro Ser Arg Phe Ser Gly Ser
            180                 185                 190 gga tct gga aca aaa ttt tct ttc aag atc agc agc cta ctg gct gaa     624
Gly Ser Gly Thr Lys Phe Ser Phe Lys Ile Ser Ser Leu Leu Ala Glu
        195                 200                 205 gat ttt gta act tat tac tgt caa caa ctc tac agt act ccg tac acg     672
Asp Phe Val Thr Tyr Tyr Cys Gln Gln Leu Tyr Ser Thr Pro Tyr Thr
    210                 215                 220 ttc gga ggg ggg aca aag ttg gaa ata aaa cgg gcg gcc gca             714
Phe Gly Gly Gly Thr Lys Leu Glu Ile Lys Arg Ala Ala Ala
225                 230                 235
```

<210> SEQ ID NO 8
<211> LENGTH: 238
<212> TYPE: PRT
<213> ORGANISM: Artificial
<220> FEATURE:
<223> OTHER INFORMATION: Synthetic Construct

<400> SEQUENCE: 8

```
Met Ala Gln Val Gln Leu Gln Gln Ser Gly Gly Gly Leu Val Gln Pro
1               5                   10                  15

Gly Gly Ser Leu Lys Leu Ser Cys Ala Ala Ser Gly Phe Thr Phe Ser
            20                  25                  30
```

```
Arg Tyr Gly Met Ser Trp Val Arg Gln Thr Pro Asp Lys Arg Leu Glu
        35                  40                  45

Leu Val Ala Thr Ile Asn Ser Asn Gly Gly Ser Thr Tyr Tyr Pro Asp
    50                  55                  60

Ser Val Lys Gly Arg Phe Thr Ile Ser Arg Asp Asn Ala Lys Asn Thr
65                  70                  75                  80

Leu Tyr Leu Gln Met Ser Ser Leu Lys Ser Ala Asp Thr Ala Met Tyr
                85                  90                  95

Phe Cys Ala Arg Gly Gly Tyr Leu Asp Tyr Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ala Asp Ile Glu Leu Thr Gln Ser Pro Ser Leu Gly Glu
130                 135                 140

Ser Val Thr Ile Thr Cys Leu Ala Ser Gln Thr Ile Gly Thr Trp Leu
145                 150                 155                 160

Ala Trp Phe Gln Gln Lys Pro Gly Lys Ser Pro Gln Leu Leu Ile Tyr
                165                 170                 175

Ala Ala Thr Ser Leu Ala Asp Gly Val Pro Ser Arg Phe Ser Gly Ser
            180                 185                 190

Gly Ser Gly Thr Lys Phe Ser Phe Lys Ile Ser Ser Leu Leu Ala Glu
        195                 200                 205

Asp Phe Val Thr Tyr Tyr Cys Gln Gln Leu Tyr Ser Thr Pro Tyr Thr
210                 215                 220

Phe Gly Gly Gly Thr Lys Leu Glu Ile Lys Arg Ala Ala Ala
225                 230                 235

<210> SEQ ID NO 9
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(15)

<400> SEQUENCE: 9 agc tat ggc atg tct                                              15
Ser Tyr Gly Met Ser
1               5

<210> SEQ ID NO 10
<211> LENGTH: 5
<212> TYPE: PRT
<213> ORGANISM: Artificial
<220> FEATURE:
<223> OTHER INFORMATION: Synthetic Construct

<400> SEQUENCE: 10

Ser Tyr Gly Met Ser
1               5

<210> SEQ ID NO 11
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(48)
```

-continued

<400> SEQUENCE: 11

```
acc att agt agt ggt ggt agt tac acc tac tat cca gac agt gtg aag      48
Thr Ile Ser Ser Gly Gly Ser Tyr Thr Tyr Tyr Pro Asp Ser Val Lys
1               5                   10                  15 ggg                                                                   51
```

<210> SEQ ID NO 12
<211> LENGTH: 16
<212> TYPE: PRT
<213> ORGANISM: Artificial
<220> FEATURE:
<223> OTHER INFORMATION: Synthetic Construct

<400> SEQUENCE: 12

```
Thr Ile Ser Ser Gly Gly Ser Tyr Thr Tyr Tyr Pro Asp Ser Val Lys
1               5                   10                  15
```

<210> SEQ ID NO 13
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(39)

<400> SEQUENCE: 13

```
cat aac tac ggt agt agc tac cct tat gct atg gac tac                   39
His Asn Tyr Gly Ser Ser Tyr Pro Tyr Ala Met Asp Tyr
1               5                   10
```

<210> SEQ ID NO 14
<211> LENGTH: 13
<212> TYPE: PRT
<213> ORGANISM: Artificial
<220> FEATURE:
<223> OTHER INFORMATION: Synthetic Construct

<400> SEQUENCE: 14

```
His Asn Tyr Gly Ser Ser Tyr Pro Tyr Ala Met Asp Tyr
1               5                   10
```

<210> SEQ ID NO 15
<211> LENGTH: 30
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(30)

<400> SEQUENCE: 15

```
agt gcc agt tca agt gtt aat tac atg cac                               30
Ser Ala Ser Ser Ser Val Asn Tyr Met His
1               5                   10
```

<210> SEQ ID NO 16
<211> LENGTH: 10
<212> TYPE: PRT
<213> ORGANISM: Artificial
<220> FEATURE:
<223> OTHER INFORMATION: Synthetic Construct

<400> SEQUENCE: 16

```
Ser Ala Ser Ser Ser Val Asn Tyr Met His
1               5                   10
```

<210> SEQ ID NO 17
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 17 gac aca tcc aaa ttg gct tct                                    21
Asp Thr Ser Lys Leu Ala Ser
1               5

<210> SEQ ID NO 18
<211> LENGTH: 7
<212> TYPE: PRT
<213> ORGANISM: Artificial
<220> FEATURE:
<223> OTHER INFORMATION: Synthetic Construct

<400> SEQUENCE: 18

Asp Thr Ser Lys Leu Ala Ser
1               5

<210> SEQ ID NO 19
<211> LENGTH: 30
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(30)

<400> SEQUENCE: 19 ccg cag tgg agt agt aac cct ccc atg acg                        30
Pro Gln Trp Ser Ser Asn Pro Pro Met Thr
1               5                   10

<210> SEQ ID NO 20
<211> LENGTH: 10
<212> TYPE: PRT
<213> ORGANISM: Artificial
<220> FEATURE:
<223> OTHER INFORMATION: Synthetic Construct

<400> SEQUENCE: 20

Pro Gln Trp Ser Ser Asn Pro Pro Met Thr
1               5                   10

<210> SEQ ID NO 21
<211> LENGTH: 15
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(15)

<400> SEQUENCE: 21 agg tat ggc atg tct                                            15
Arg Tyr Gly Met Ser
1               5

<210> SEQ ID NO 22

```
<211> LENGTH: 5
<212> TYPE: PRT
<213> ORGANISM: Artificial
<220> FEATURE:
<223> OTHER INFORMATION: Synthetic Construct

<400> SEQUENCE: 22

Arg Tyr Gly Met Ser
1               5

<210> SEQ ID NO 23
<211> LENGTH: 51
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(51)

<400> SEQUENCE: 23 acc att aat agt aat ggc ggt agc acc tat tat cca gac agt gtg aag        48
Thr Ile Asn Ser Asn Gly Gly Ser Thr Tyr Tyr Pro Asp Ser Val Lys
1               5                   10                  15 ggc                                                                    51
Gly

<210> SEQ ID NO 24
<211> LENGTH: 17
<212> TYPE: PRT
<213> ORGANISM: Artificial
<220> FEATURE:
<223> OTHER INFORMATION: Synthetic Construct

<400> SEQUENCE: 24

Thr Ile Asn Ser Asn Gly Gly Ser Thr Tyr Tyr Pro Asp Ser Val Lys
1               5                   10                  15

Gly

<210> SEQ ID NO 25
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(18)

<400> SEQUENCE: 25 gga ggt tac ctt gac tac                                                18
Gly Gly Tyr Leu Asp Tyr
1               5

<210> SEQ ID NO 26
<211> LENGTH: 6
<212> TYPE: PRT
<213> ORGANISM: Artificial
<220> FEATURE:
<223> OTHER INFORMATION: Synthetic Construct

<400> SEQUENCE: 26

Gly Gly Tyr Leu Asp Tyr
1               5

<210> SEQ ID NO 27
<211> LENGTH: 33
<212> TYPE: DNA
```

<213> ORGANISM: Artificial
<220> FEATURE:
<223> OTHER INFORMATION: Synthetic
<220> FEATURE:
<221> NAME/KEY: CDS
<222> LOCATION: (1)..(33)

<400> SEQUENCE: 27 ctg gca agt cag acc att ggt aca tgg tta gca                    33
Leu Ala Ser Gln Thr Ile Gly Thr Trp Leu Ala
1               5                   10

<210> SEQ ID NO 28
<211> LENGTH: 11
<212> TYPE: PRT
<213> ORGANISM: Artificial
<220> FEATURE:
<223> OTHER INFORMATION: Synthetic Construct

<400> SEQUENCE: 28

Leu Ala Ser Gln Thr Ile Gly Thr Trp Leu Ala
1               5                   10

<210> SEQ ID NO 29
<211> LENGTH: 21
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(21)

<400> SEQUENCE: 29 gct gca acc agc ttg gca gat                                    21
Ala Ala Thr Ser Leu Ala Asp
1               5

<210> SEQ ID NO 30
<211> LENGTH: 7
<212> TYPE: PRT
<213> ORGANISM: Artificial
<220> FEATURE:
<223> OTHER INFORMATION: Synthetic Construct

<400> SEQUENCE: 30

Ala Ala Thr Ser Leu Ala Asp
1               5

<210> SEQ ID NO 31
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: CDS
<222> LOCATION: (1)..(27)

<400> SEQUENCE: 31 caa caa ctc tac agt act ccg tac acg                            27
Gln Gln Leu Tyr Ser Thr Pro Tyr Thr
1               5

<210> SEQ ID NO 32
<211> LENGTH: 9
<212> TYPE: PRT
<213> ORGANISM: Artificial
<220> FEATURE:
<223> OTHER INFORMATION: Synthetic Construct

<400> SEQUENCE: 32

Gln Gln Leu Tyr Ser Thr Pro Tyr Thr
1               5

<210> SEQ ID NO 33
<211> LENGTH: 4
<212> TYPE: PRT
<213> ORGANISM: Artificial
<220> FEATURE:
<223> OTHER INFORMATION: Synthetic

<400> SEQUENCE: 33

Glu Phe Arg His
1

<210> SEQ ID NO 34
<211> LENGTH: 23
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Residue at postion 1 can be C or G
<220> FEATURE:
<221> NAME/KEY: misc_feature
<222> LOCATION: (3)..(3)
<223> OTHER INFORMATION: Residue at postion 3 can be either A or C or G
      or T.
<220> FEATURE:
<221> NAME/KEY: misc_feature
<222> LOCATION: (4)..(4)
<223> OTHER INFORMATION: Residue at postion 4 can be either A or G.
<220> FEATURE:
<221> NAME/KEY: misc_feature
<222> LOCATION: (6)..(6)
<223> OTHER INFORMATION: Residue at postion 6 can be either C or G or T.
<220> FEATURE:
<221> NAME/KEY: misc_feature
<222> LOCATION: (7)..(7)
<223> OTHER INFORMATION: Residue at postion 7 can be either A or C.
<220> FEATURE:
<221> NAME/KEY: misc_feature
<222> LOCATION: (9)..(9)
<223> OTHER INFORMATION: Residue at postion 9 can be either A or G.
<220> FEATURE:
<221> NAME/KEY: misc_feature
<222> LOCATION: (10)..(10)
<223> OTHER INFORMATION: Residue at postion 10 can be either C or T.
<220> FEATURE:
<221> NAME/KEY: misc_feature
<222> LOCATION: (12)..(12)
<223> OTHER INFORMATION: Residue at postion 12 can be either G or T.
<220> FEATURE:
<221> NAME/KEY: misc_feature
<222> LOCATION: (13)..(13)
<223> OTHER INFORMATION: Residue at postion 13 can be either C or G.
<220> FEATURE:
<221> NAME/KEY: misc_feature
<222> LOCATION: (14)..(14)
<223> OTHER INFORMATION: Residue at postion 14 can be either A or T.
<220> FEATURE:
<221> NAME/KEY: misc_feature
<222> LOCATION: (19)..(19)
<223> OTHER INFORMATION: Residue at postion 19 can be either C or T.
<220> FEATURE:
<221> NAME/KEY: misc_feature
<222> LOCATION: (21)..(21)
<223> OTHER INFORMATION: Residue at postion 21 can be either A or T.

<400> SEQUENCE: 34
sanrtbmary tkswgsagyc wgg                                        23

<210> SEQ ID NO 35
<211> LENGTH: 24
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: Residue at postiion 3 can be either A or C.
<220> FEATURE:
<221> NAME/KEY: misc_feature
<222> LOCATION: (4)..(4)
<223> OTHER INFORMATION: Residue at postion 4 can be either A or G.
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (15)..(15)
<223> OTHER INFORMATION: Residue at postion 15 can be either C or G.
<220> FEATURE:
<221> NAME/KEY: misc_feature
<222> LOCATION: (16)..(16)
<223> OTHER INFORMATION: Residue at postion 16 can be either A or C or T.
<220> FEATURE:
<221> NAME/KEY: misc_feature
<222> LOCATION: (17)..(17)
<223> OTHER INFORMATION: Residue at postion 17 can be either A or G.
<220> FEATURE:
<221> NAME/KEY: misc_feature
<222> LOCATION: (18)..(18)
<223> OTHER INFORMATION: Residue at postion 17 can be either A or G or T.
<220> FEATURE:
<221> NAME/KEY: misc_feature
<222> LOCATION: (19)..(19)
<223> OTHER INFORMATION: Residue at postion 17 can be either A or C or G.
<220> FEATURE:
<221> NAME/KEY: misc_feature
<222> LOCATION: (21)..(21)
<223> OTHER INFORMATION: Residue at postion 21 can be either C or G or T.

<400> SEQUENCE: 35
tgmrgagacn gtgashrdvg tbcc                                            24

<210> SEQ ID NO 36
<211> LENGTH: 23
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (4)..(4)
<223> OTHER INFORMATION: Residue at postiion 4 can be either A or G.
<220> FEATURE:
<221> NAME/KEY: misc_feature
<222> LOCATION: (6)..(6)
<223> OTHER INFORMATION: Residue at postiion 6 can be either C or T.
<220> FEATURE:
<221> NAME/KEY: misc_feature
<222> LOCATION: (7)..(7)
<223> OTHER INFORMATION: Residue at postiion 7 can be either G or T.
<220> FEATURE:
<221> NAME/KEY: misc_feature
<222> LOCATION: (10)..(10)
<223> OTHER INFORMATION: Residue at postion 10 can be either A or C.
<220> FEATURE:

```
<221> NAME/KEY: misc_feature
<222> LOCATION: (12)..(12)
<223> OTHER INFORMATION: Residue at postion 12 can be either C or G.
<220> FEATURE:
<221> NAME/KEY: misc_feature
<222> LOCATION: (15)..(15)
<223> OTHER INFORMATION: Residue at postion 15 can be either A or C or
      G.
<220> FEATURE:
<221> NAME/KEY: misc_feature
<222> LOCATION: (18)..(18)
<223> OTHER INFORMATION: Residue at postion 18 can be either A or G.
<220> FEATURE:
<221> NAME/KEY: misc_feature
<222> LOCATION: (19)..(19)
<223> OTHER INFORMATION: Residue at postion 19 can be either A or G or
      T.
<220> FEATURE:
<221> NAME/KEY: misc_feature
<222> LOCATION: (22)..(22)
<223> OTHER INFORMATION: Residue at postion 22 can be either A or C.

<400> SEQUENCE: 36
ganrtyktgm tsacvcardc tmc                                           23

<210> SEQ ID NO 37
<211> LENGTH: 24
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Residue at postion 1 can be either A or C.
<220> FEATURE:
<221> NAME/KEY: misc_feature
<222> LOCATION: (4)..(4)
<223> OTHER INFORMATION: Residue at postion 4 can be either A or T.
<220> FEATURE:
<221> NAME/KEY: misc_feature
<222> LOCATION: (7)..(7)
<223> OTHER INFORMATION: Residue at postion 7 can be either C or G or T.
<220> FEATURE:
<221> NAME/KEY: misc_feature
<222> LOCATION: (9)..(9)
<223> OTHER INFORMATION: Residue at postion 9 can be either G or T.
<220> FEATURE:
<221> NAME/KEY: misc_feature
<222> LOCATION: (10)..(10)
<223> OTHER INFORMATION: Residue at postion 10 can be either C or T.
<220> FEATURE:
<221> NAME/KEY: misc_feature
<222> LOCATION: (15)..(15)
<223> OTHER INFORMATION: Residue at postion 15 can be either A or G.
<220> FEATURE:
<221> NAME/KEY: misc_feature
<222> LOCATION: (16)..(16)
<223> OTHER INFORMATION: Residue at postion 16 can be either C or G.
<220> FEATURE:
<221> NAME/KEY: misc_feature
<222> LOCATION: (19)..(19)
<223> OTHER INFORMATION: Residue at postion 19 can be either G or T.
<220> FEATURE:
<221> NAME/KEY: misc_feature
<222> LOCATION: (22)..(22)
<223> OTHER INFORMATION: Residue at postion 22 can be either C or G.

<400> SEQUENCE: 37
mcgwttbaky tccarsttkg tscc                                          24

<210> SEQ ID NO 38
<211> LENGTH: 30
<212> TYPE: DNA
<213> ORGANISM: Artificial
<220> FEATURE:
```

```
<223> OTHER INFORMATION: Synthetic
<220> FEATURE:
<221> NAME/KEY: misc_feature
<222> LOCATION: (13)..(13)
<223> OTHER INFORMATION: Residue at postion 13 can be either C or G.
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (16)..(16)
<223> OTHER INFORMATION: Residue at postion 16 can be either A or G.
<220> FEATURE:
<221> NAME/KEY: misc_feature
<222> LOCATION: (18)..(18)
<223> OTHER INFORMATION: Residue at postion 18 can be either C or G or
      T.
<220> FEATURE:
<221> NAME/KEY: misc_feature
<222> LOCATION: (19)..(19)
<223> OTHER INFORMATION: Residue at postion 19 can be either A or C.
<220> FEATURE:
<221> NAME/KEY: misc_feature
<222> LOCATION: (21)..(21)
<223> OTHER INFORMATION: Residue at postion 21 can be either A or G.
<220> FEATURE:
<221> NAME/KEY: misc_feature
<222> LOCATION: (22)..(22)
<223> OTHER INFORMATION: Residue at postion 22 can be either C or T.
<220> FEATURE:
<221> NAME/KEY: misc_feature
<222> LOCATION: (24)..(24)
<223> OTHER INFORMATION: Residue at postion 24 can be either G or T.
<220> FEATURE:
<221> NAME/KEY: misc_feature
<222> LOCATION: (25)..(25)
<223> OTHER INFORMATION: Residue at postion 25 can be either C or G.
<220> FEATURE:
<221> NAME/KEY: misc_feature
<222> LOCATION: (26)..(26)
<223> OTHER INFORMATION: Residue at postion 26 can be either A or T.
<220> FEATURE:
<221> NAME/KEY: misc_feature
<222> LOCATION: (28)..(28)
<223> OTHER INFORMATION: Residue at postion 28 can be either C or G.

<400> SEQUENCE: 38
catgccatgg ctsanrtbma rytkswgsag                                           30

<210> SEQ ID NO 39
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (16)..(16)
<223> OTHER INFORMATION: Residue at postion 16 can be either A or C.
<220> FEATURE:
<221> NAME/KEY: misc_feature
<222> LOCATION: (19)..(19)
<223> OTHER INFORMATION: Residue at postion 19 can be either A or T.
<220> FEATURE:
<221> NAME/KEY: misc_feature
<222> LOCATION: (22)..(22)
<223> OTHER INFORMATION: Residue at postion 22 can be either C or G or
      T.
<220> FEATURE:
<221> NAME/KEY: misc_feature
<222> LOCATION: (24)..(24)
<223> OTHER INFORMATION: Residue at postion 24 can be either G or T.
<220> FEATURE:
<221> NAME/KEY: misc_feature
<222> LOCATION: (25)..(25)
<223> OTHER INFORMATION: Residue at postion 25 can be either C or T.
<220> FEATURE:
```

<221> NAME/KEY: misc_feature
<222> LOCATION: (31)..(31)
<223> OTHER INFORMATION: Residue at postion 31 can be either C or G.

<400> SEQUENCE: 39
atagaatgcg gccgcmcgwt tbakytccar stt         33

<210> SEQ ID NO 40
<211> LENGTH: 18
<212> TYPE: DNA
<213> ORGANISM: Artificial
<220> FEATURE:
<223> OTHER INFORMATION: Synthetic

<400> SEQUENCE: 40
catatggctc atgtccag         18

<210> SEQ ID NO 41
<211> LENGTH: 21
<212> TYPE: DNA
<213> ORGANISM: Artificial
<220> FEATURE:
<223> OTHER INFORMATION: Synthetic

<400> SEQUENCE: 41
ctcgagtgca gagacggtga c         21

<210> SEQ ID NO 42
<211> LENGTH: 24
<212> TYPE: DNA
<213> ORGANISM: Artificial
<220> FEATURE:
<223> OTHER INFORMATION: Synthetic

<400> SEQUENCE: 42
catatggaga taatgataac gcag         24

<210> SEQ ID NO 43
<211> LENGTH: 21
<212> TYPE: DNA
<213> ORGANISM: Artificial
<220> FEATURE:
<223> OTHER INFORMATION: Synthetic

<400> SEQUENCE: 43
ctcgaggcgt ttcatctcca g         21